(12) United States Patent
Wang et al.

(10) Patent No.: US 10,548,543 B2
(45) Date of Patent: Feb. 4, 2020

(54) SPECTRAL CT SYSTEMS AND METHODS

(71) Applicant: RENSSELAER POLYTECHNIC INSTITUTE, Troy, NY (US)

(72) Inventors: Ge Wang, Loudonville, NY (US); Yan Xi, Syracuse, NY (US); Wenxiang Cong, Albany, NY (US); Zaifeng Shi, Tianjin (CN)

(73) Assignee: Rensselaer Polytechnic Institute, Troy, NY (US)

( * ) Notice: Subject to any disclaimer, the term of this patent is extended or adjusted under 35 U.S.C. 154(b) by 233 days.

(21) Appl. No.: 15/538,376

(22) PCT Filed: Dec. 22, 2015

(86) PCT No.: PCT/US2015/067441
§ 371 (c)(1),
(2) Date: Jun. 21, 2017

(87) PCT Pub. No.: WO2016/106348
PCT Pub. Date: Jun. 30, 2016

(65) Prior Publication Data
US 2017/0360385 A1 Dec. 21, 2017

Related U.S. Application Data

(60) Provisional application No. 62/095,235, filed on Dec. 22, 2014.

(51) Int. Cl.
*A61B 6/00* (2006.01)
*A61B 6/03* (2006.01)
*G01T 1/29* (2006.01)

(52) U.S. Cl.
CPC ............ *A61B 6/4233* (2013.01); *A61B 6/032* (2013.01); *A61B 6/4241* (2013.01); *A61B 6/4266* (2013.01); *A61B 6/4275* (2013.01); *A61B 6/4291* (2013.01); *A61B 6/482* (2013.01);
(Continued)

(58) Field of Classification Search
CPC ..... A61B 6/4233; A61B 6/032; A61B 6/4241; A61B 6/4266; A61B 6/4275; A61B 6/4291; A61B 6/482; A61B 6/5205; A61B 6/5217; G01T 1/2985
See application file for complete search history.

(56) References Cited

U.S. PATENT DOCUMENTS 5,493,122 A   2/1996   Farr
6,331,705 B1  12/2001  Eisen et al.
(Continued)

OTHER PUBLICATIONS

T.G. Schmidt, "Optimal image-based weighting for energy-resolved CT", 2009, Medical Physics, vol. 36, No. 7, pp. 3018-3027. (Year: 2009).*

(Continued)

*Primary Examiner* — Kiho Kim
(74) *Attorney, Agent, or Firm* — Murtha Cullina LLP

(57) ABSTRACT

Novel and advantageous methods and systems for performing spectral computed tomography are provided. An edge-on detector, such as a silicon strip detector, can be used to receive X-rays after passing through a sample to be imaged. An energy resolving process can be performed on the collected X-ray radiation. The CT scanner can have third-generation or fourth-generation geometry.

24 Claims, 30 Drawing Sheets

(52) U.S. Cl.
CPC .......... *A61B 6/5205* (2013.01); *A61B 6/5217* (2013.01); *G01T 1/2985* (2013.01)

(56) References Cited

U.S. PATENT DOCUMENTS

| | | | | |
|---|---|---|---|---|
| 7,271,468 | B2* | 9/2007 | Holland | H01L 27/1463 257/400 |
| 8,183,535 | B2* | 5/2012 | Danielsson | G01T 1/243 250/370.09 |
| 2003/0164442 | A1* | 9/2003 | Beusch | H04N 5/32 250/208.1 |
| 2009/0080597 | A1 | 3/2009 | Basu | |
| 2010/0215230 | A1 | 8/2010 | Bornefalk et al. | |
| 2012/0326045 | A1 | 12/2012 | Seino et al. | |
| 2016/0106387 | A1* | 4/2016 | Kahn | A61B 6/5211 378/62 |

OTHER PUBLICATIONS

International Search Report/Written Opinion, PCT International Application No. PCT/US2015/067441, PCT/ISA/210, PCT/ISA/237, dated May 4, 2016.
Bertolini et al., "Semiconductor Detectors," Science, Apr. 1970, p. 462, vol. 168.
Pan et al., "Computed tomography in color: nanok-enhanced spectral CT molecular imaging," Angewandte Chemie International Edition in English, Dec. 2010, Author Manuscript, pp. 1-11, vol. 49, No. 50.
Chu et al., "Combination of current-integrating/photon-counting detector modules for spectral CT," Physics in Medicine and Biology, Sep. 2013, pp. 7009-7024, vol. 58.
Shikhaliev, "Projection x-ray imaging with photon energy weighting: experimental evaluation with a prototype detector," Physics in Medicine and Biology, Jul. 2009, pp. 4971-4992, vol. 54.
Shikhaliev, "Energy-resolved computed tomography: first experimental results," Physics in Medicine and Biology, Sep. 2008, pp. 5595-5613, vol. 53.
Burke et aL, "CCD soft x-ray imaging spectrometer for the ASCA satellite," IEEE Transactions on Nuclear Science, Feb. 1994, pp. 375-385, vol. 41, No. 1.
Lundqvist et al., "Computer simulations and performance measurements on a silicon strip detector for edge-on Imaging," 1999 IEEE Nuclear Science Symposium Conference, Oct. 1999, pp. 433-438, Seattle, Washington.
Hoople et al., "Characteristics of submicrometer gaps in buried-channel CCD structures," IEEE Transactions on Electron Devices, May 1991, pp. 1175-1181, vol. 38, No. 5.
Arfelli et al., "An 'edge-on' silicon strip detector for x-ray imaging," IEEE Transactions on Nuclear Science, Jun. 1997, pp. 874-880, vol. 44, No. 3.
Overdick et al., "Status of direct conversion detectors for medical imaging with x-rays," IEEE Transactions on Nuclear Science, Aug. 2009, pp. 1800-1809, vol. 56, No. 4.
Doran et al., "A CCD-based optical CT scanner for high-resolution 3D imaging of radiation dose distributions: equipment specifications, optical simulations and preliminary results," Physics in Medicine and Biology, Nov. 2001, pp. 3191-3213, vol. 46.
Taguchi et al., "Vision 20/20: single photon counting x-ray detectors in medical imaging," Medical Physics, Sep. 2013, pp. 1-19, vol. 40, No. 10.
Bornefalk et al., "Photon-counting spectral computed tomography using silicon strip detectors: a feasibility study," Physics in Medicine and Biology, Mar. 2010, pp. 1999-2022, vol. 55.
Persson et al., "Energy-resolved CT imaging with a photon-counting silicon-strip detector," Physics in Medicine and Biology, Oct. 2014, pp. 6709-6727, vol. 59.
Gruner et al., "Charge-coupled device area x-ray detectors," Review of Scientific Instruments, Aug. 2002, pp. 2815-2842, vol. 73, No. 8.
Alvarez et al., "Energy-selective reconstructions in x-ray computerized tomography," Physics in Medicine and Biology, Sep. 1976, pp. 733-744, vol. 21, No. 5.
Giersch et al., "The influence of energy weighting on x-ray imaging quality," Nuclear Instruments and Methods in Physics Research Section A, Sep. 2004, pp. 68-74, vol. 531.
Taguchi et al., "An analytical model of the effects of pulse pileup on the energy spectrum recorded by energy resolved photon counting x-ray detectors," Medical Physics, Jul. 2010, pp. 3957-3969, vol. 37, No. 8.
Marcelot et al., "Study of CCD transport on CMOS imaging technology: comparison between SCCD and BCCD, and ramp effect on the CTI," IEEE Transactions on Electron Devices, Mar. 2014, pp. 844-849, vol. 61.
Tompsett, "Surface potential equilibration method of setting charge in charge-coupled devices," IEEE Transactions om Electron Devices, Jun. 1975, pp. 305-309, vol. 22, No. 6.
Rigon et al., "A single-photon counting 'edge-on' silicon detector for synchrotron radiation mammography," Nuclear Instruments and Methods in Physics Research A, Sep. 2009, pp. S62-S65, vol. 608.

* cited by examiner

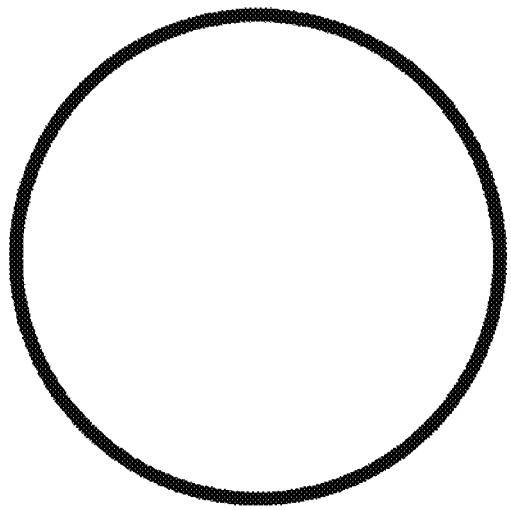
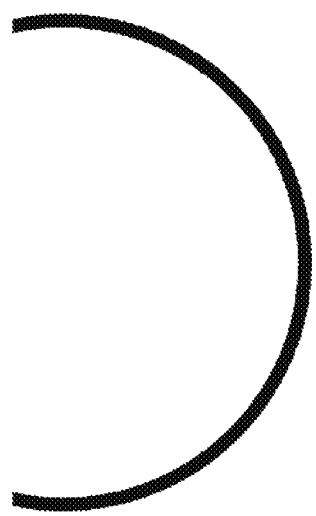
Figure 17A						Figure 17B
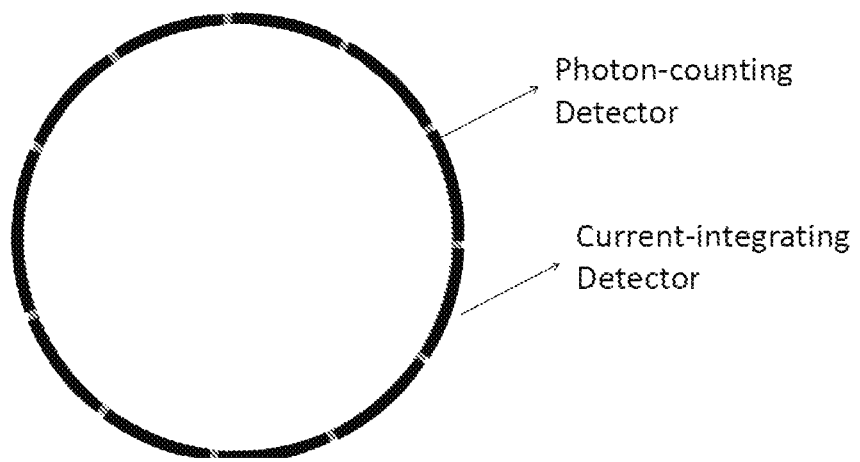
Figure 18

SPECTRAL CT SYSTEMS AND METHODS

CROSS-REFERENCE TO RELATED APPLICATIONS

The present application is a national stage application of International Patent Application No. PCT/US2015/067441, filed Dec. 22, 2015, which claims the benefit of U.S. Provisional Application Ser. No. 62/095,235, filed Dec. 22, 2014, both of which are incorporated herein by reference in their entireties including any figures, tables, and drawings.

BACKGROUND OF INVENTION

Computed Tomography (CT) is a major tool in diagnostic imaging. X-ray detection technology typically uses energy-integrating detectors that add electrical signals, from interactions between an X-ray beam and a material of the detector, over the whole spectrum. Energy-integrating detectors often lose spectral information. Spectral CT (SCT) has advantages over conventional CT by offering detailed spectral information for material decomposition. SCT can also reduce beam-hardening artifacts and radiation dose. However, related art SCT is slower, less stable, and much more expensive than conventional CT.

BRIEF SUMMARY

The subject invention provides novel and advantageous methods and systems for performing imaging, such as spectral computed tomography imaging. An edge-on detector, such as a silicon strip detector, can be used to receive X-rays after passing through a sample to be imaged. An energy resolving process can be performed on the collected charges of the collected X-ray radiation. The CT scanner can have third-generation or fourth-generation geometry.

In an embodiment, a method of imaging can include: providing X-ray radiation to a sample to be imaged; collecting the X-ray radiation with a detector; and performing an energy resolving process on the collected X-ray radiation. The energy resolving process can include determining the generated charge density within the detector and repeating the determination of the generated charge density at a different thickness within the material of the detector.

In another embodiment, a (non-transitory) machine-readable medium (e.g., a computer-readable medium) can include machine-executable (e.g., computer-executable) instructions for performing the energy resolving process described herein.

In another embodiment, an imaging system can include: a computed tomography scanner including an X-ray source; a detector for receiving X-ray radiation from the X-ray source after it passes through a sample to be imaged; and a machine-readable medium (e.g., a computer-readable medium) having machine-executable (e.g., computer-executable) instructions for performing the energy resolving process described herein.

BRIEF DESCRIPTION OF THE DRAWINGS

FIG. 5 shows a schematic view of a fixed random-thresholding detector with two slip rings at different speeds. If the X-ray tube slip ring speed is X1 Hz, and the X-ray detector slip ring speed is X2 Hz, with X1>X2 or X1<X2, then the maximum turn number N can be determined from:

$$\frac{(N + \alpha/2\pi)}{X1} = \frac{N}{X2}.$$

Figure 6:
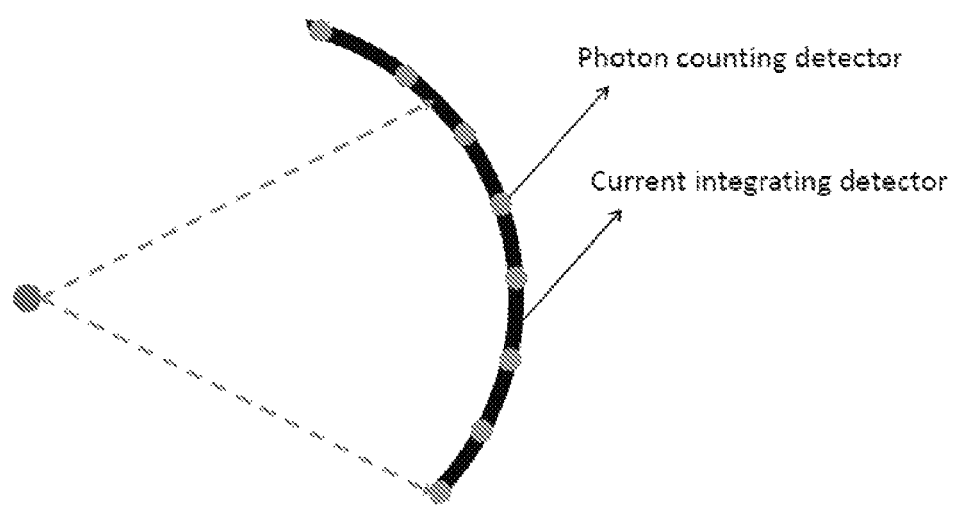

FIG. 6 shows a schematic view of a fixed random-thresholding detector with two slip rings at different speeds, and also with a sparsely distributed photon counting detector.

Figure 7:
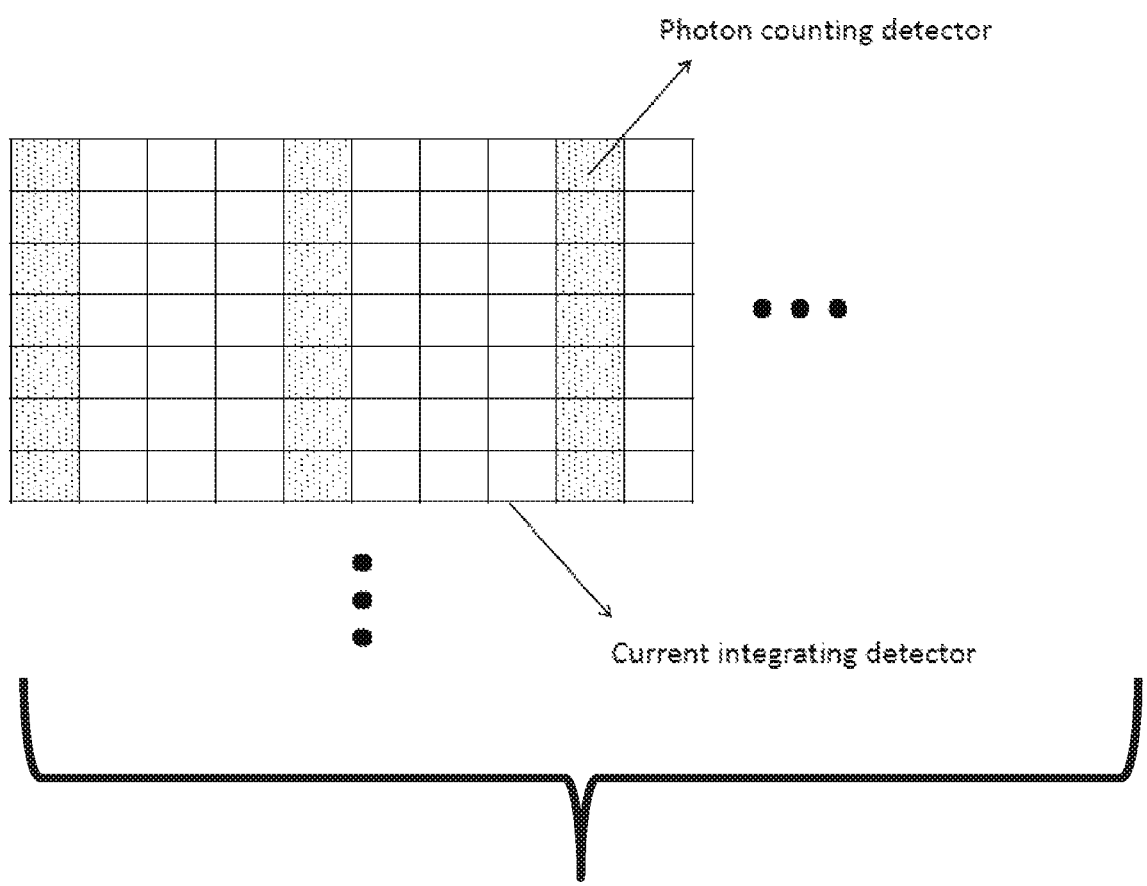

FIG. 7 shows a representative view of a current integrating detector and photon counting detector.

Figure 8:
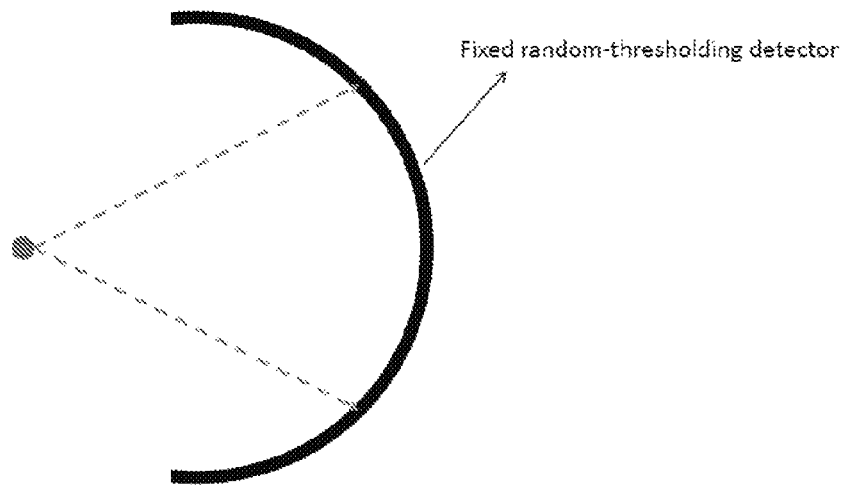

FIG. 8 shows a schematic view of a fixed random-thresholding detector with a fourth-generation SCT scanner, including a fixed detector array and a half ring.

Figure 9:
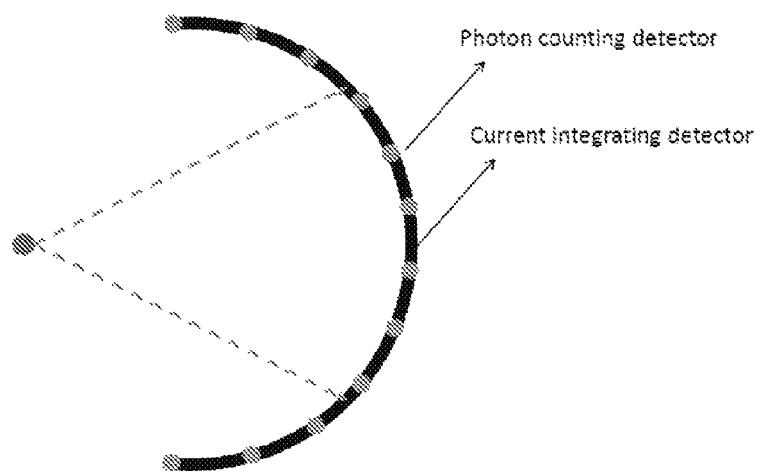

FIG. 9 shows a schematic view of a fixed random-thresholding detector with a fourth-generation SCT scanner, including a fixed detector array, a half ring, and a sparsely distributed photon counting detector.

Figure 10:
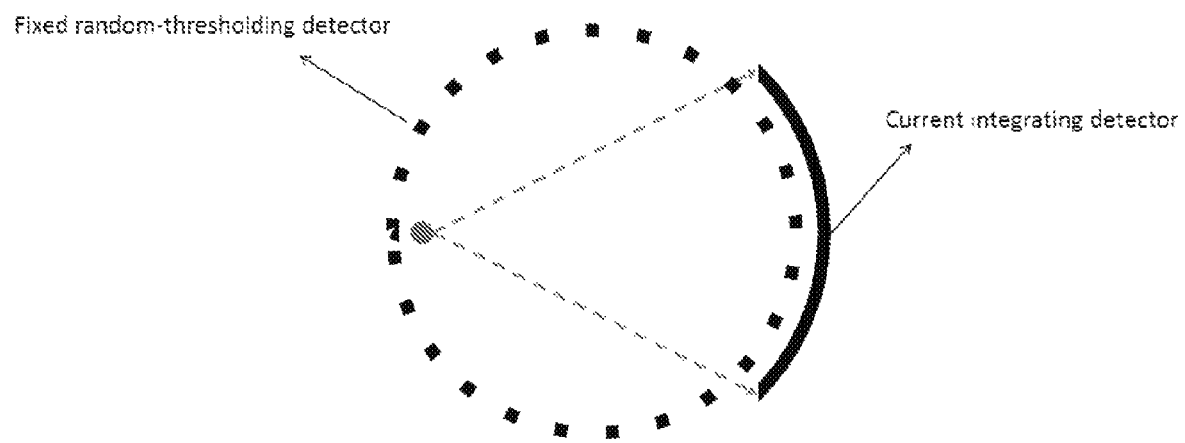

FIG. 10 shows a schematic view of a sparsely distributed random-thresholding detector, with a third-generation SCT scanner, along a full ring.

Figure 11:
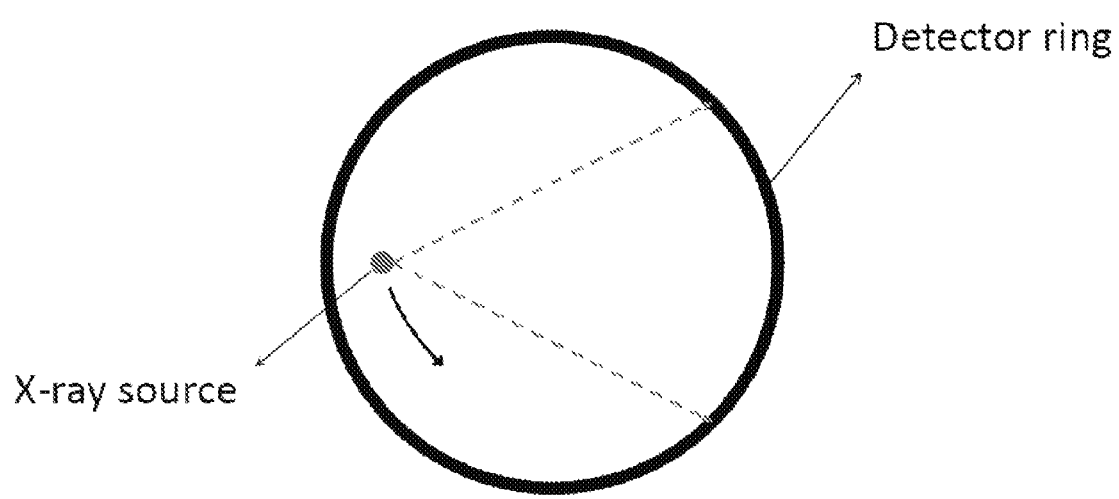

FIG. 11 shows a top view of a single X-ray source and detector geometry.

Figure 12:
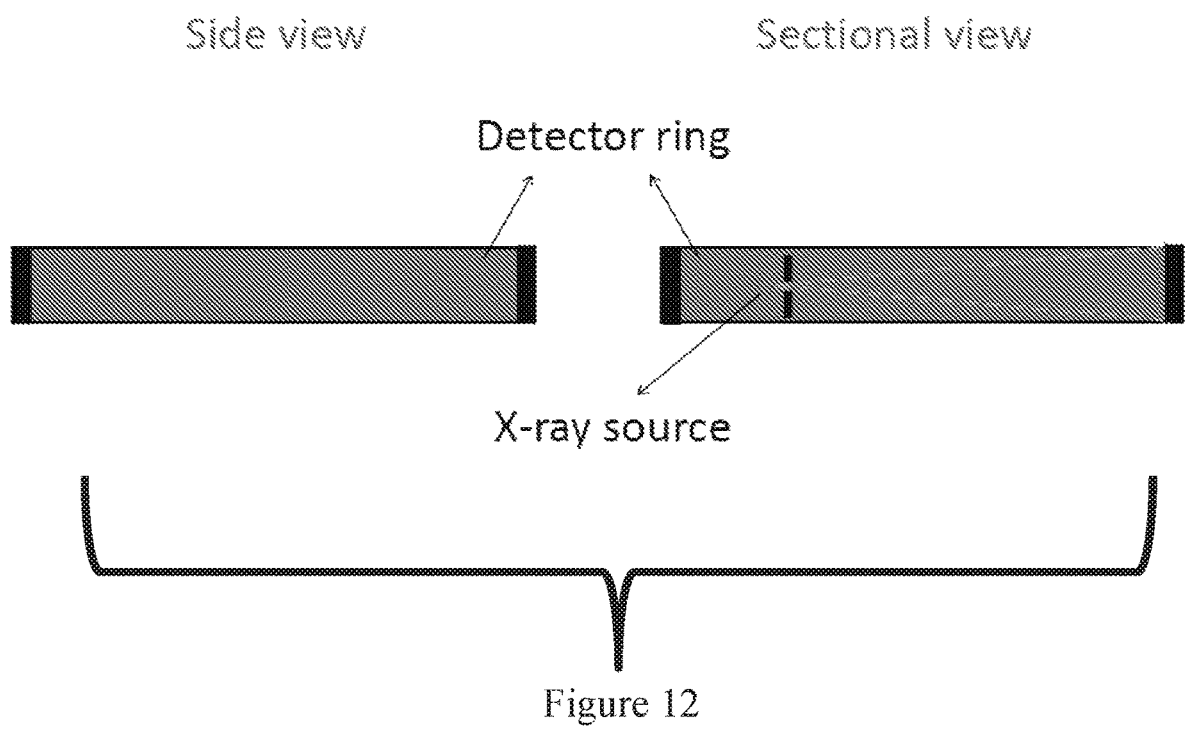

FIG. 12 shows a side view and sectional view of third-generation CT geometry.

Figure 13:
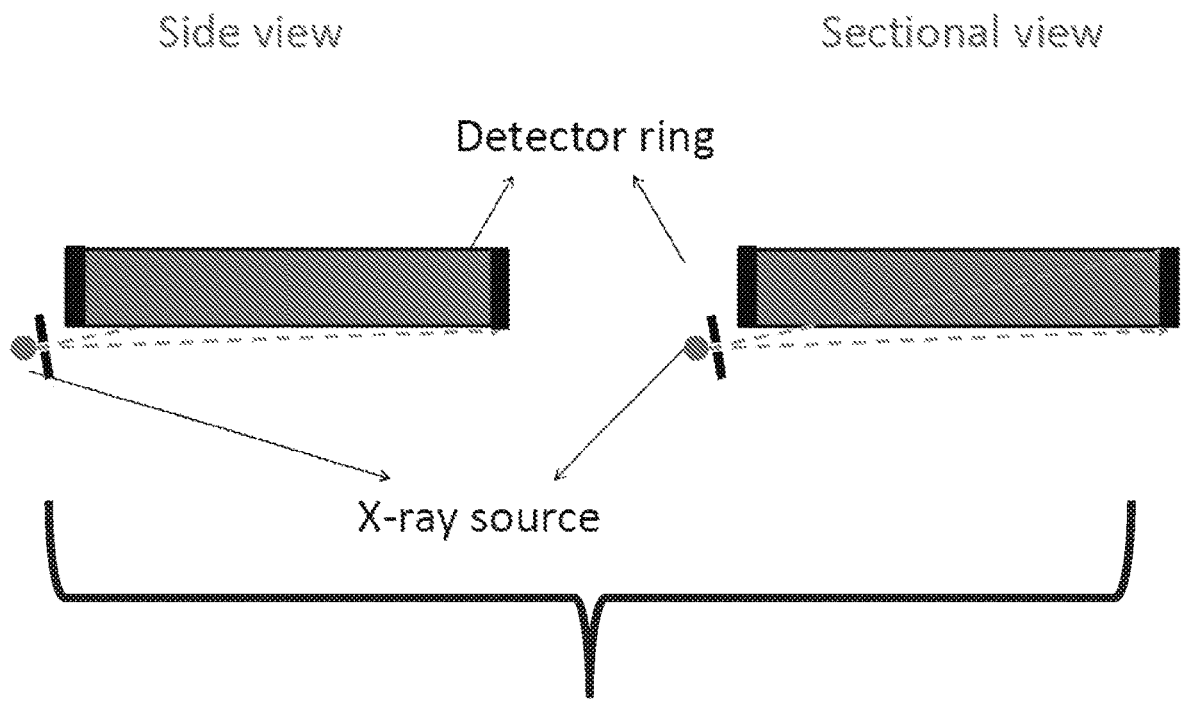

FIG. 13 shows a side view and sectional view of third-generation CT geometry with two slip rings at different speeds.

Figure 14:
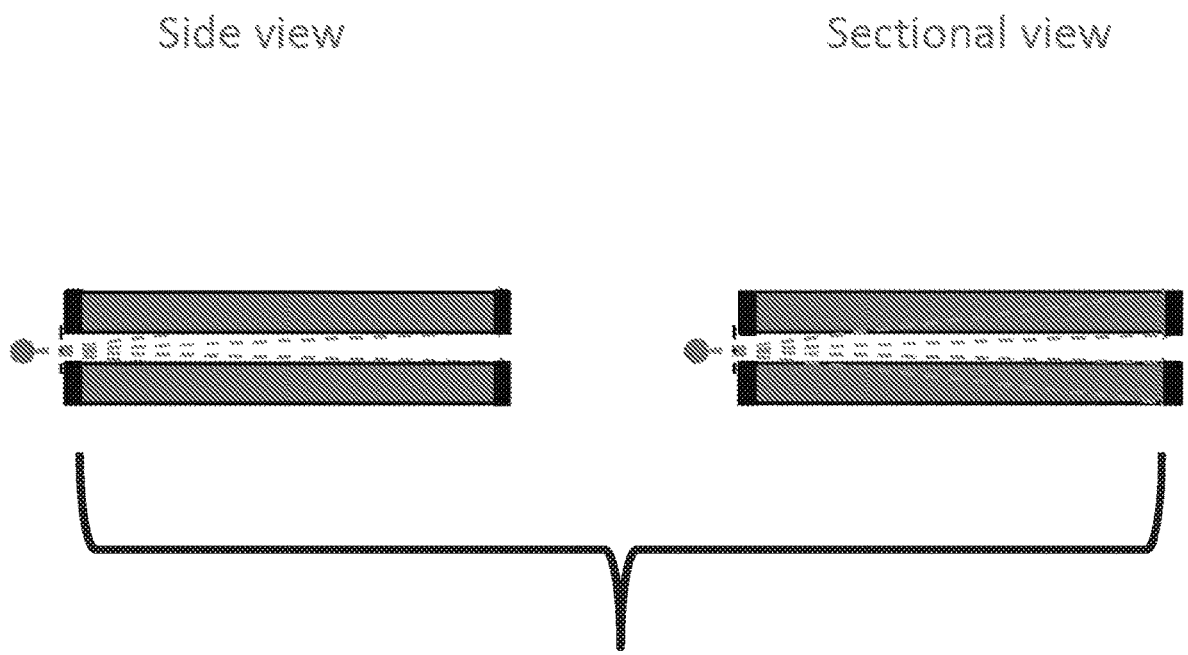

FIG. 14 shows a side view and sectional view of third-generation CT geometry with two slip rings at different speeds.

Figure 15:
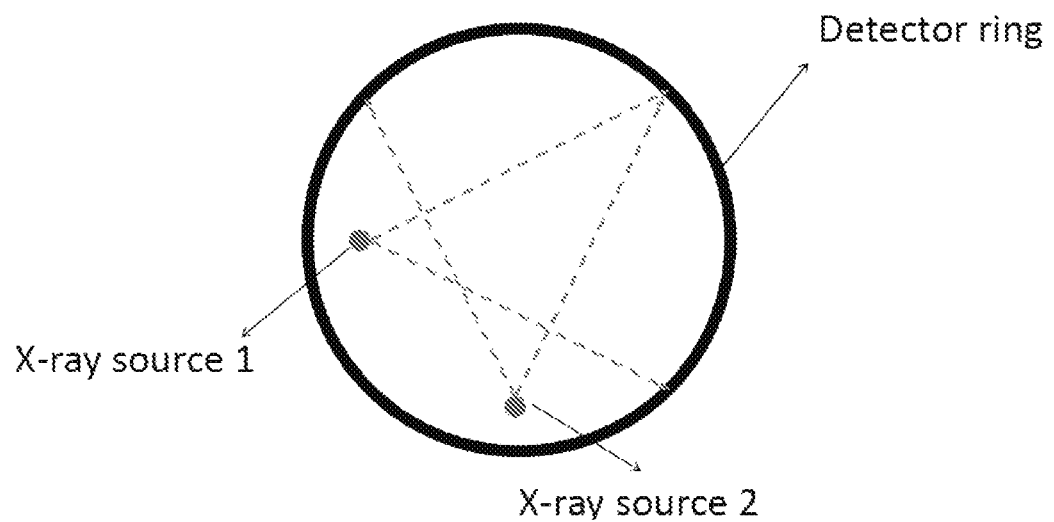

FIG. 15 shows a top view of dual X-ray sources and detector geometry.

Figure 16:
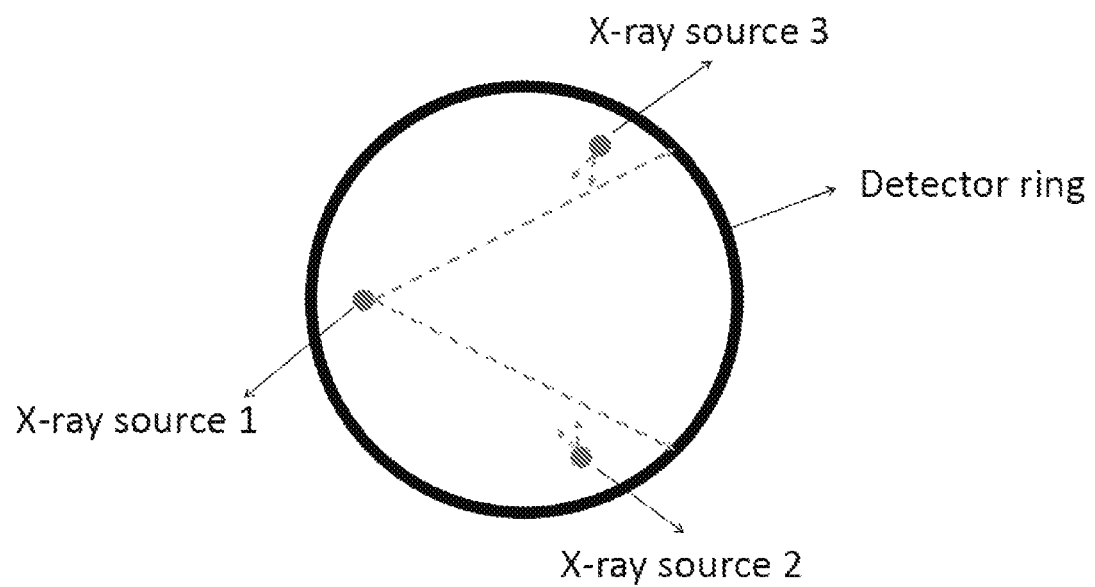

FIG. 16 shows a top view of triple X-ray sources and detector geometry.

FIG. 17A shows a schematic view of a fill ring detector ring design.

FIG. 17B shows a schematic view of a half ring detector ring design.

FIG. 18 shows a schematic view of a current-integrating and photon-counting detector combination.

Figure 19:
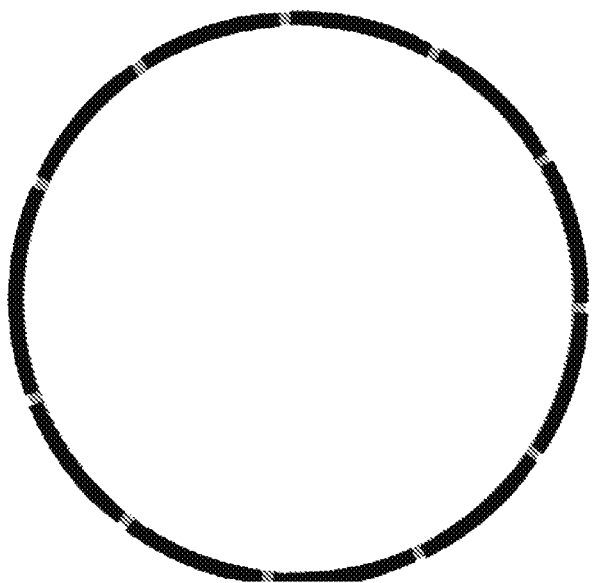

FIG. 19 shows a schematic view of a current-integrating and photon-counting detector combination.

Figure 20:
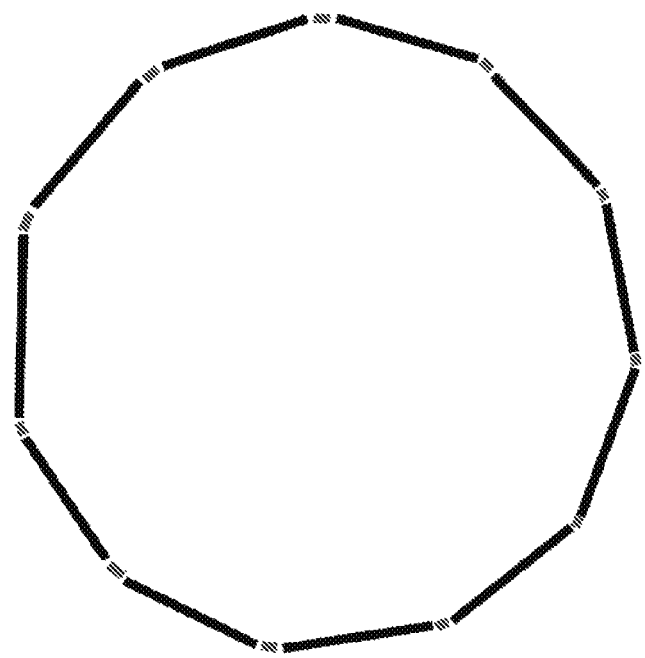

FIG. 20 shows a schematic view of a current-integrating and photon-counting detector combination.

Figure 21:
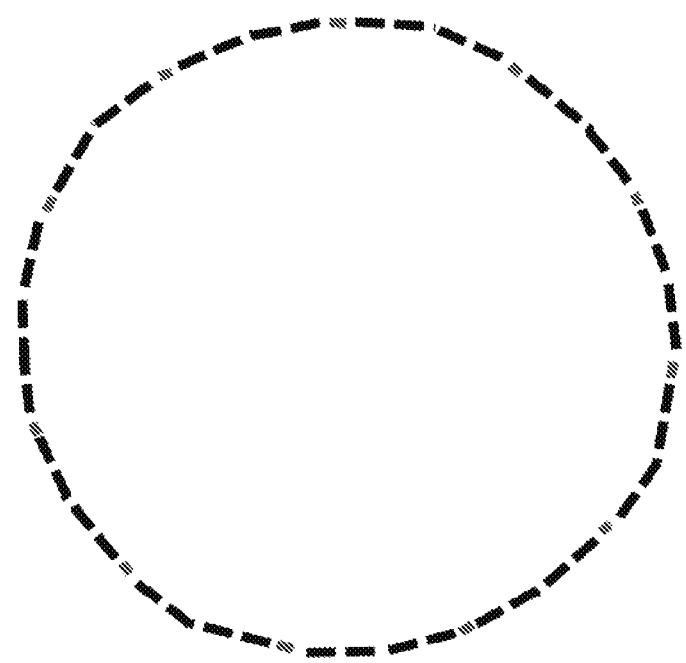

FIG. 21 shows a schematic view of a current-integrating and photon-counting detector combination.

Figure 22A:
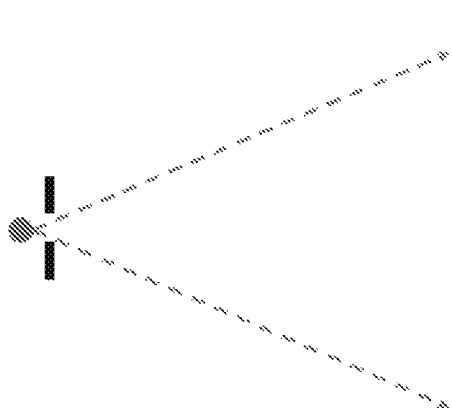

FIG. 22A shows a schematic view of a single-beam pre-collimator design.

Figure 22B:
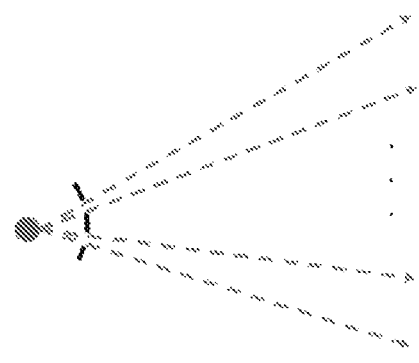

FIG. 22B shows a schematic view of a multiple-beam pre-collimator design.

Figures 23A, 23B:
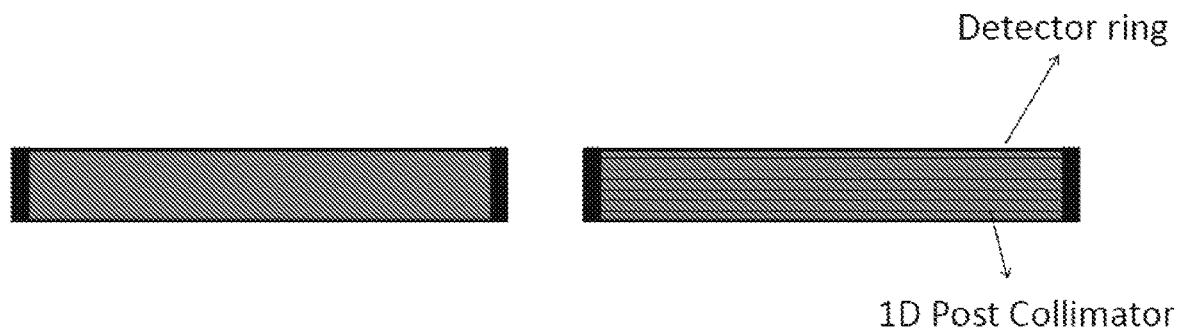

FIG. 23A shows a schematic view of a design with no post-collimator.

FIG. 23B shows a schematic view of a post-collimator design.

Figure 24:
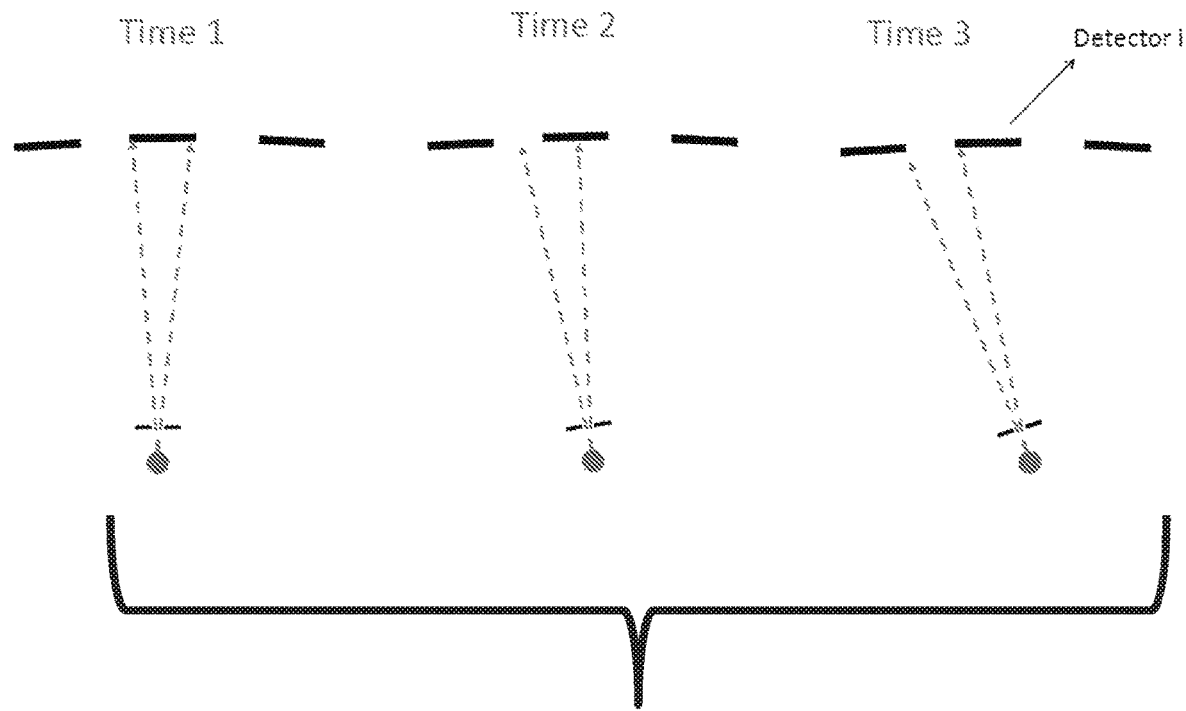

FIG. 24 shows a schematic view of a software and hardware method for detection. Only part of the detector ring and one narrow X-ray beam can be shown, if desired.

Figure 25A:
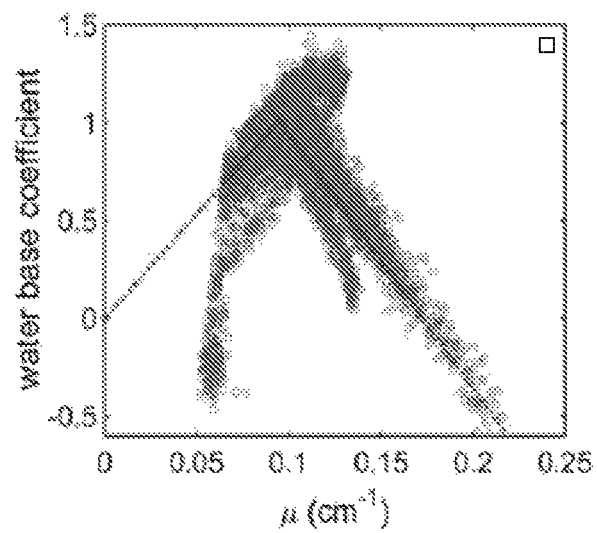

FIG. 25A shows a plot of water base coefficient versus μ for basis material coefficient reconstruction.

Figure 25B:
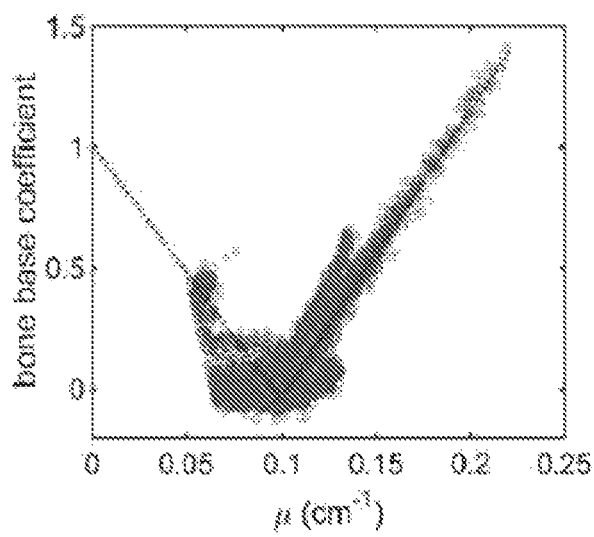

FIG. 25B shows a plot of bone base coefficient versus μ for basis material coefficient reconstruction.

Figure 25C:
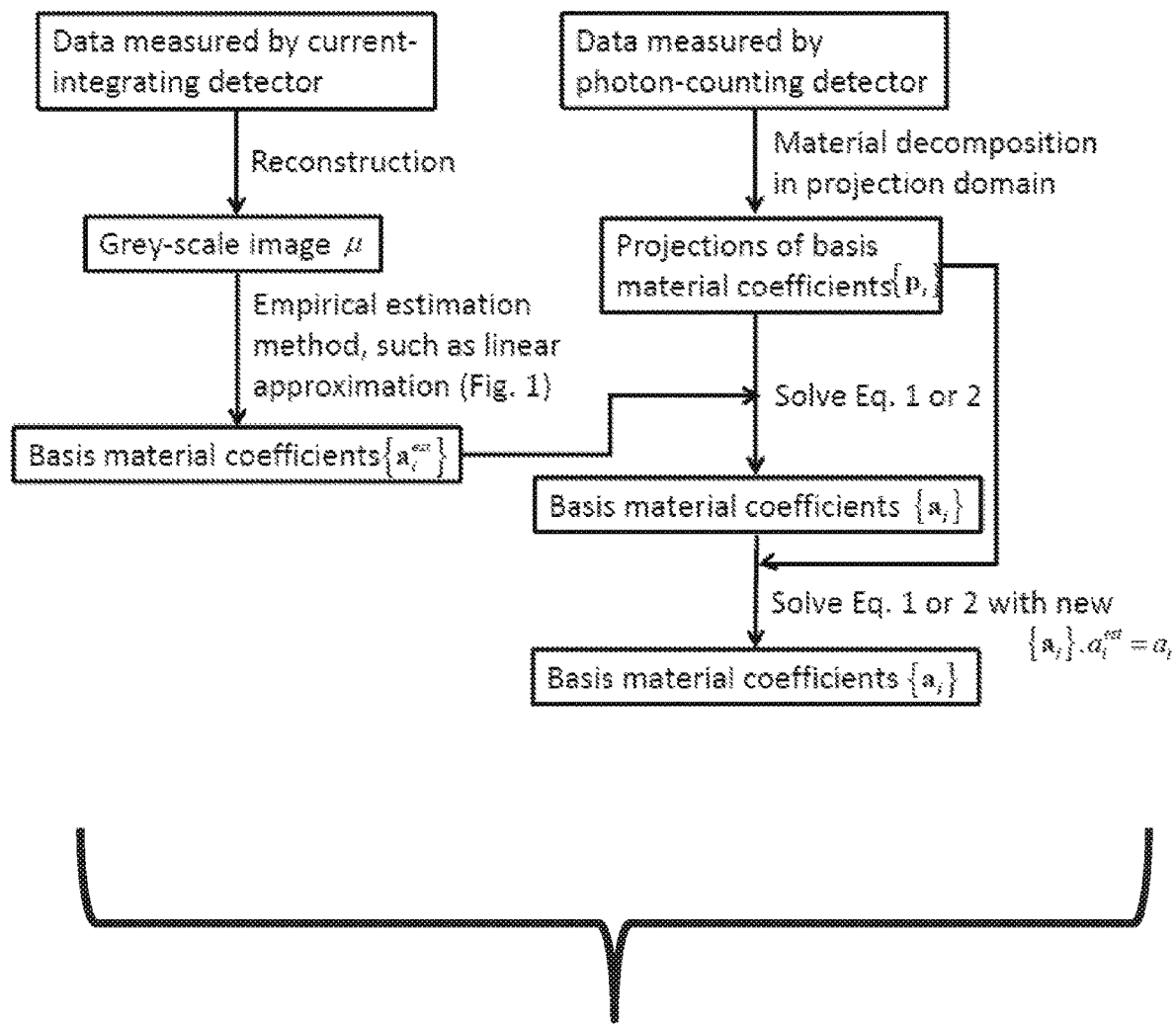

FIG. 25C shows a flow chart for basis material coefficient reconstruction.

Figure 26A:
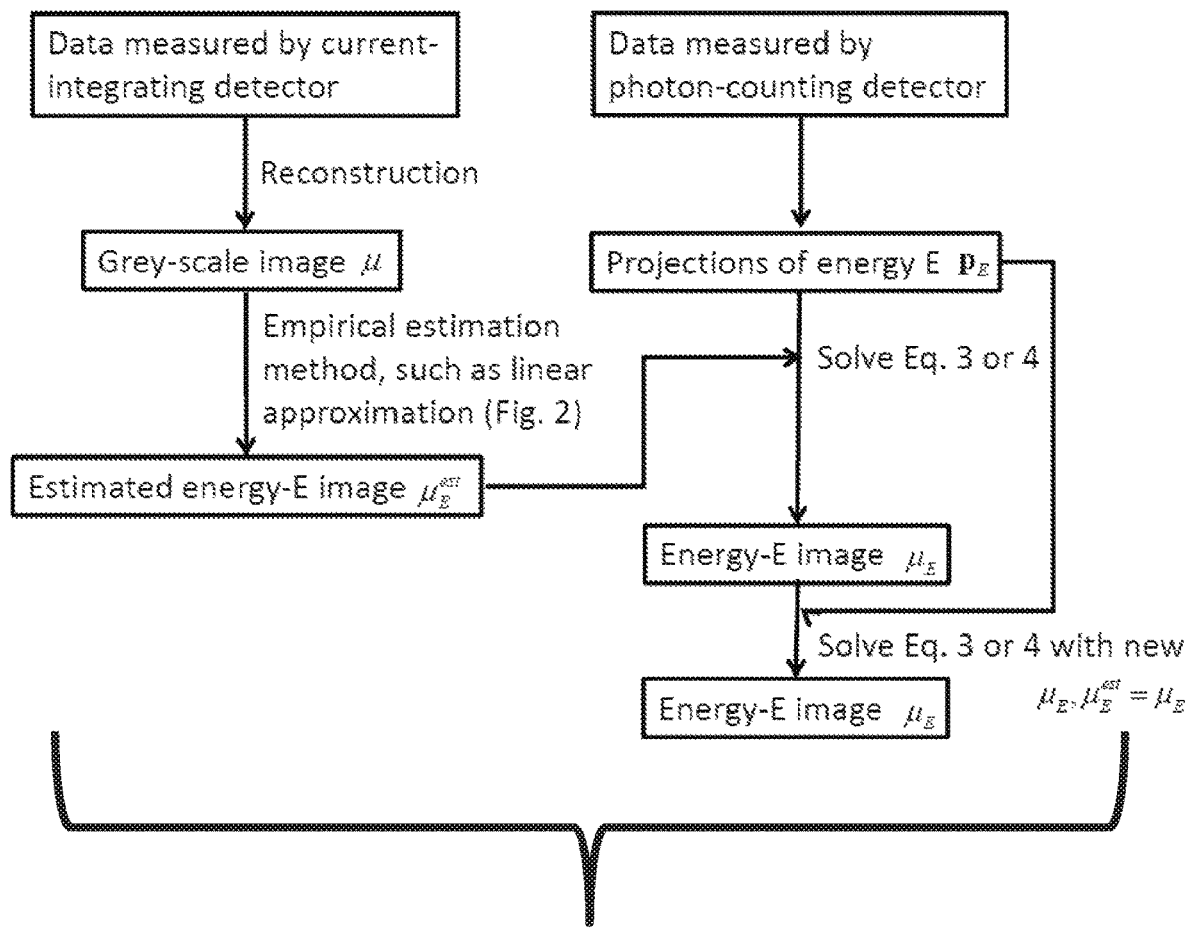

FIG. 26A shows a flow chart for specific energy image reconstruction.

Figure 26B:
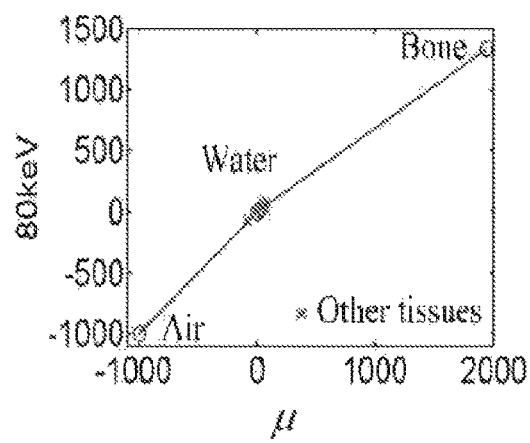

FIG. 26B shows a plot for specific energy image reconstruction.

Figure 27:
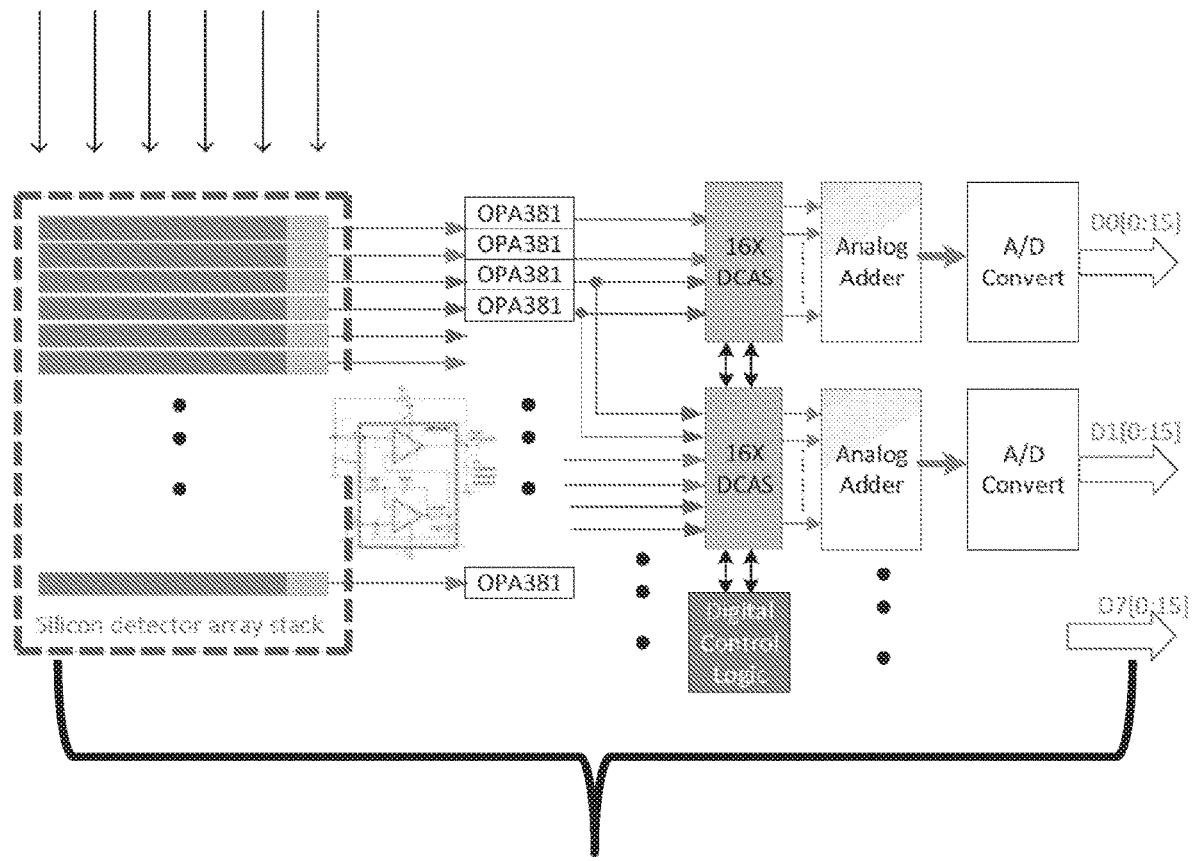

FIG. 27 shows a schematic view of an X-ray detector.

Figure 28:
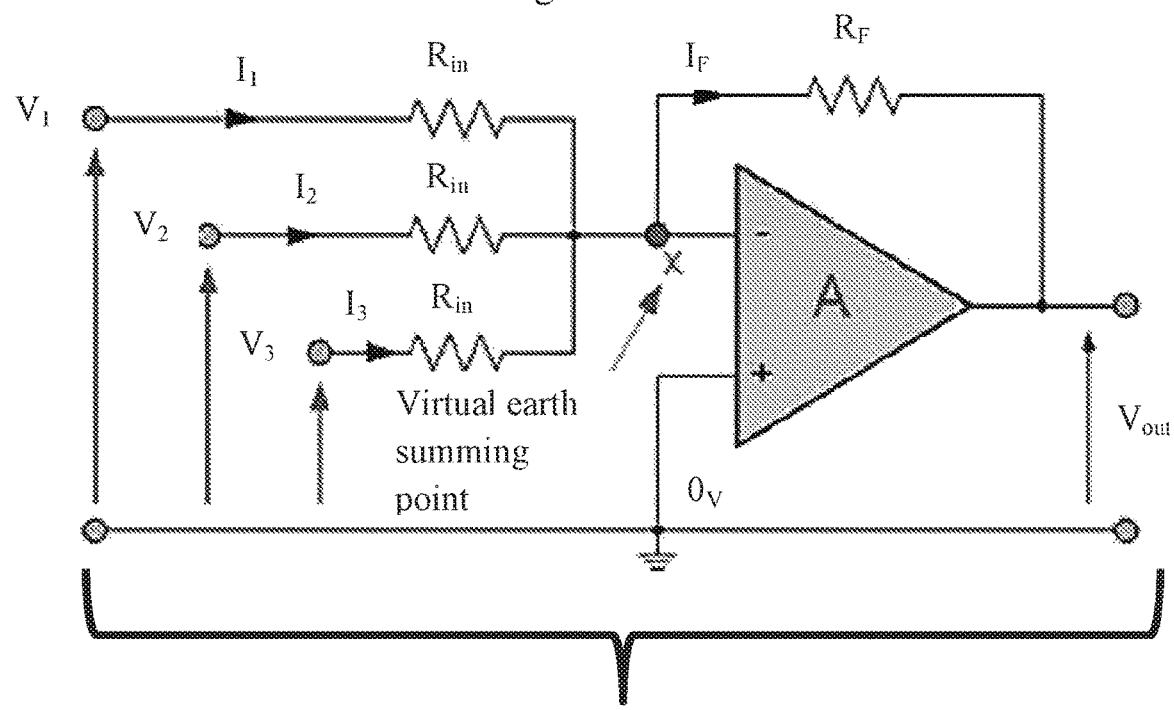

FIG. 28 shows a schematic view of an operational amplifier and negative feedback circuit.

Figure 29A:
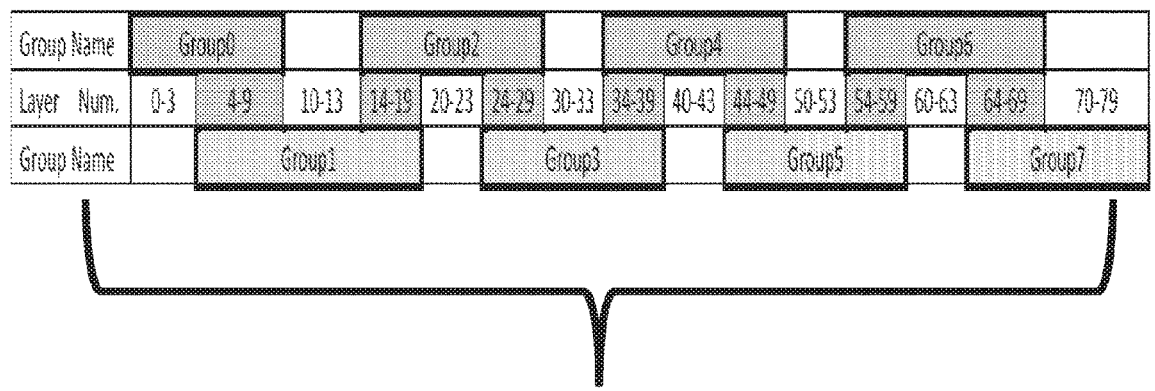

FIG. 29A shows a listing of groups for 80 detector layers.

Figure 29B:
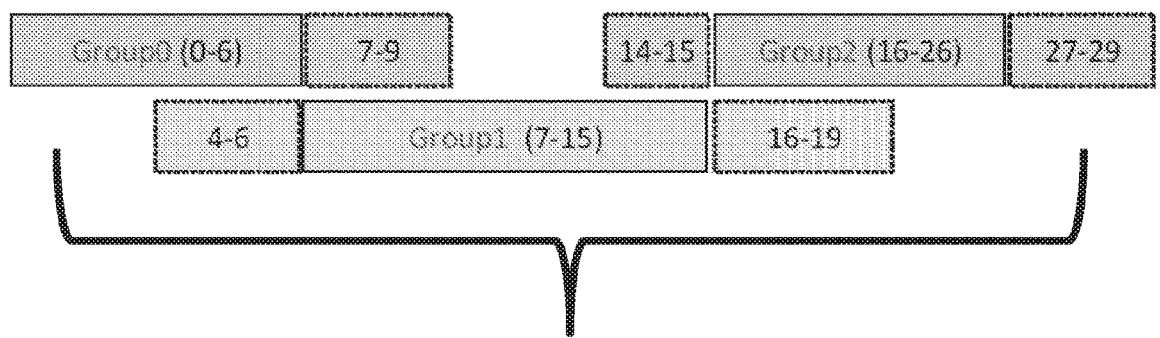
Figure 30:
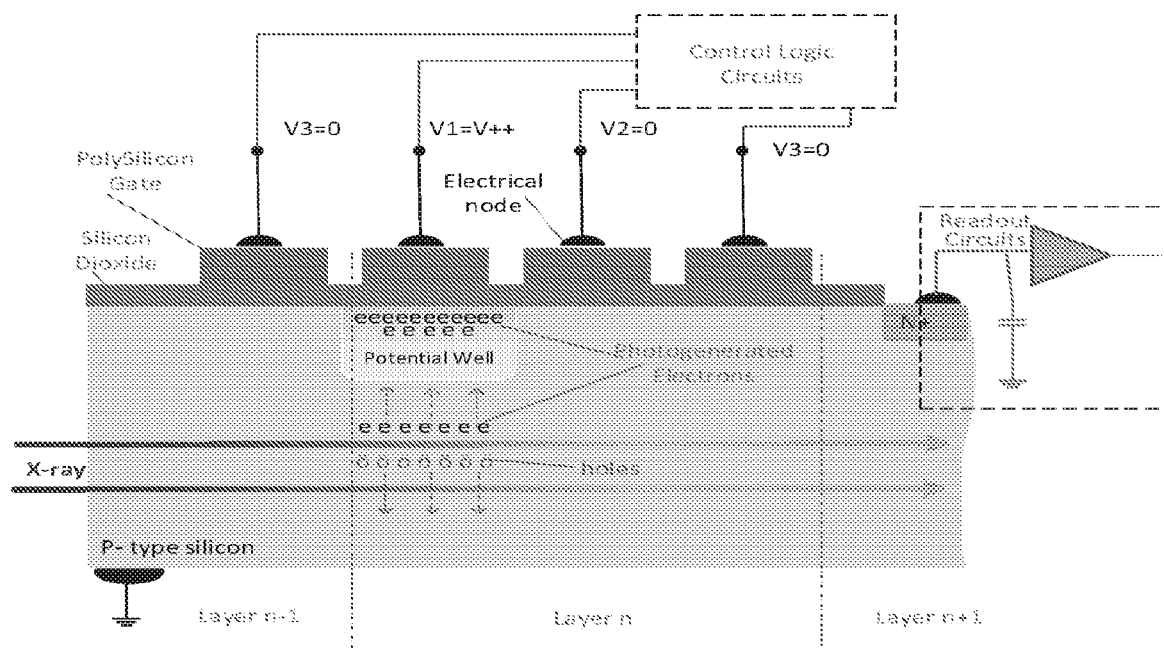

FIG. 29B shows a listing of an example grouping style for groups 0 and group 1 of FIG. 29A FIG. 30 shows a schematic view of an edge-on photon absorption scheme and device according to an embodiment of the subject invention.

Figure 31:
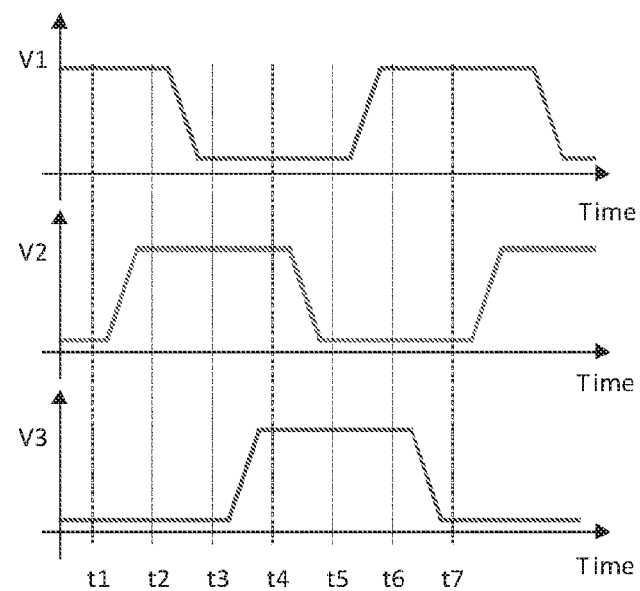

FIG. 31 shows plot of voltage versus time for charge transfer logic.

Figure 32:
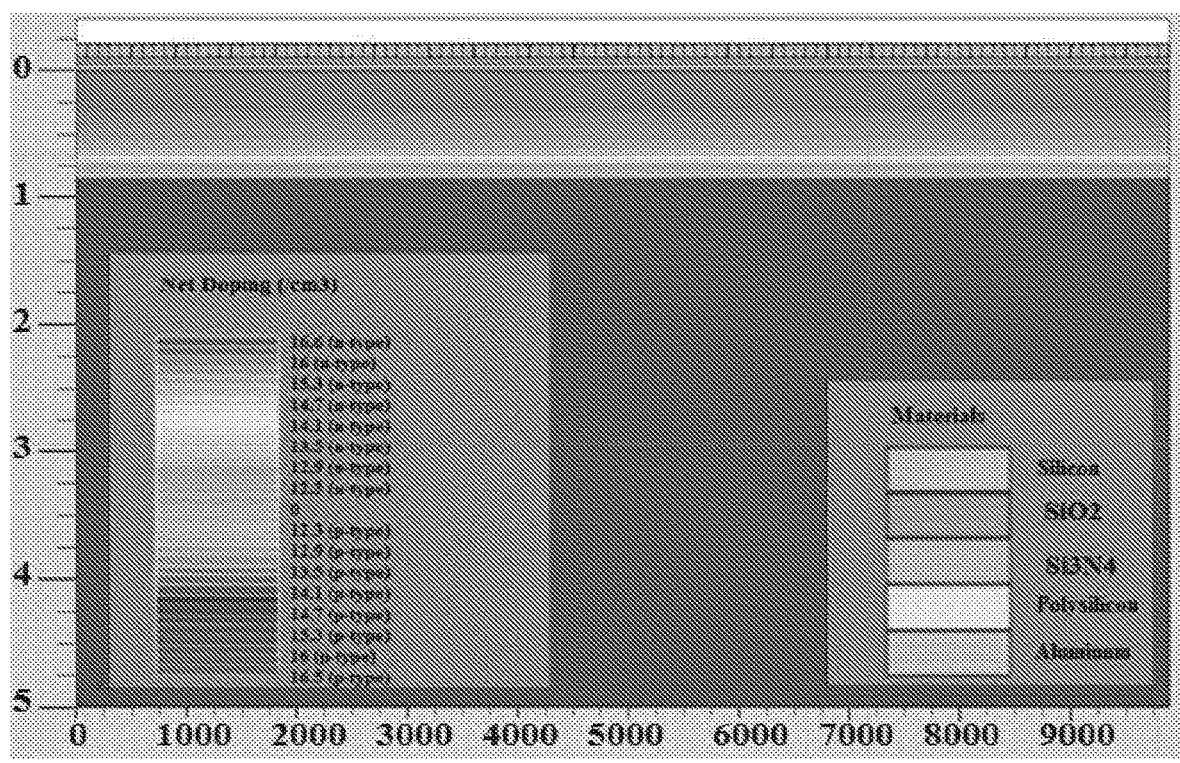

FIG. 32 shows a simulation image for device modeling with net doping.

Figure 33:
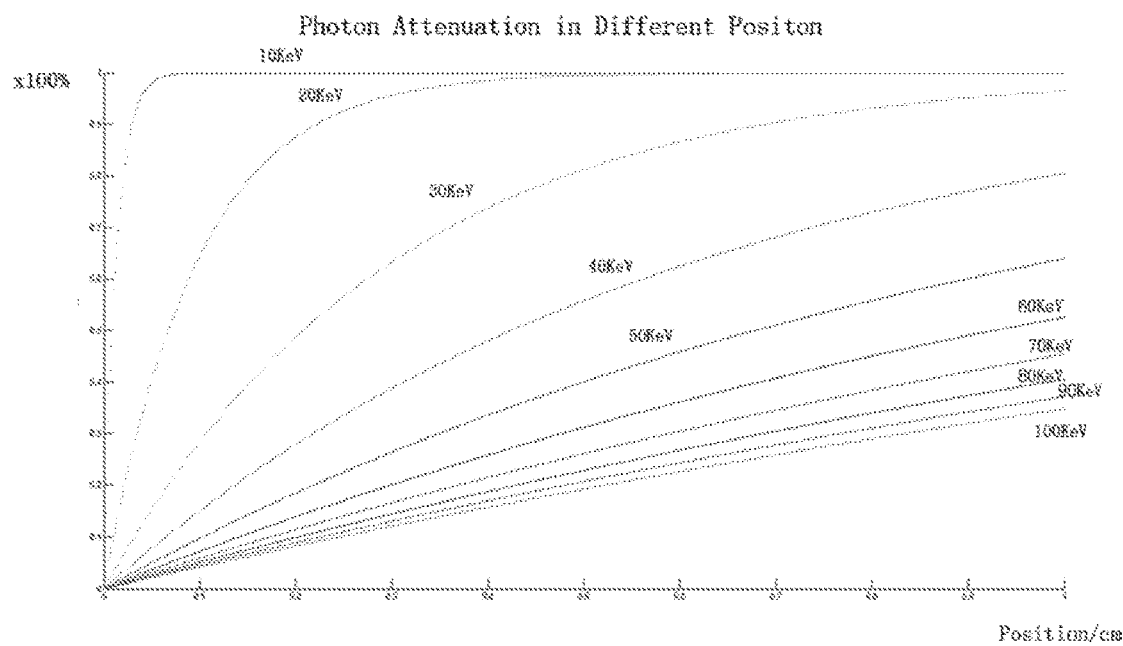

FIG. 33 shows a plot of attenuation versus position at different energies, illustrating photon attenuation.

Figure 34A:
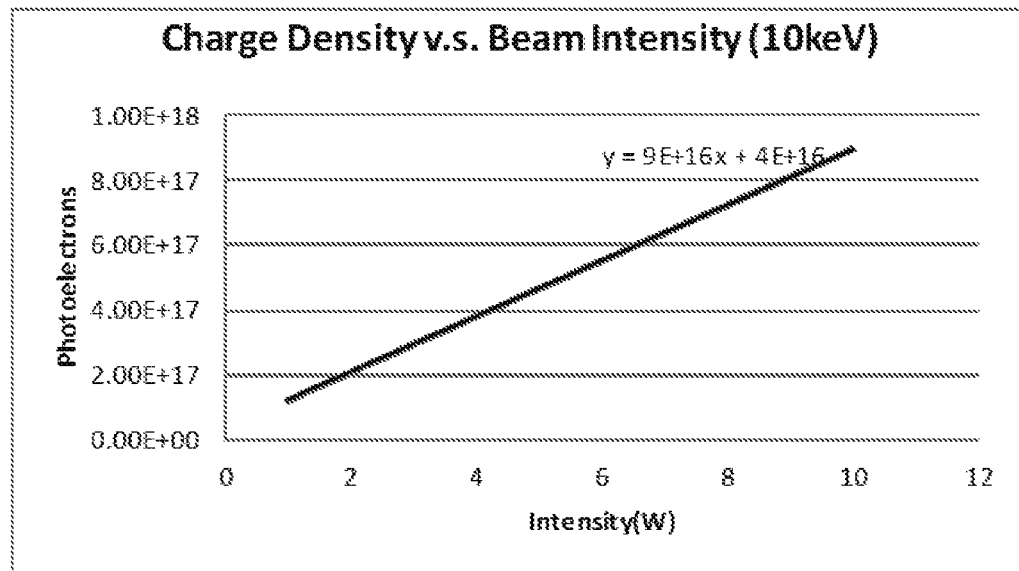

FIG. 34A shows a plot of number of generated photoelectrons versus beam intensity (in Watts (W)) as a charge response of monochromatic radiation at 10 keV.

Figure 34B:
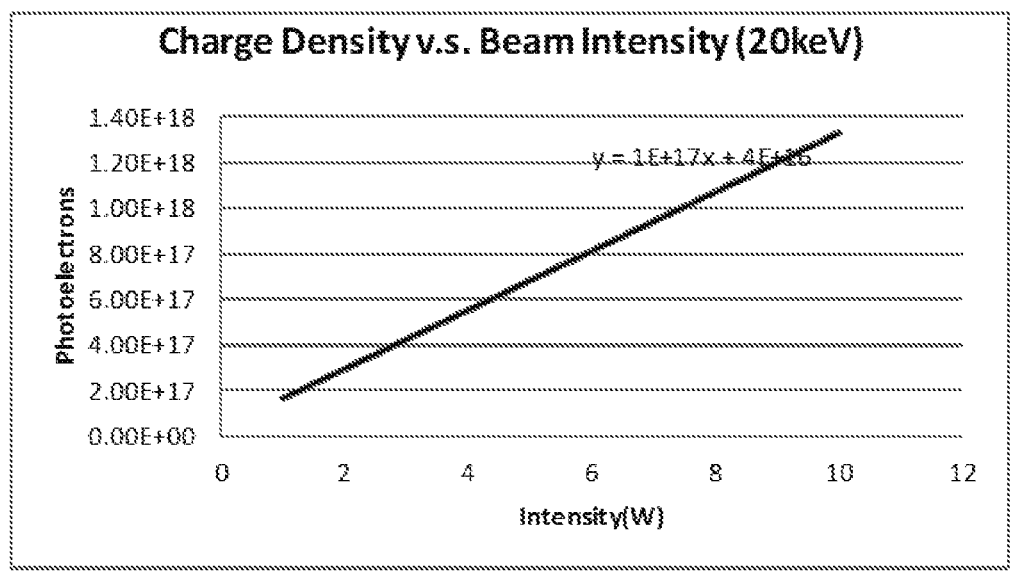

FIG. 34B shows a plot of number of generated photoelectrons versus beam intensity (in W) as a charge response of monochromatic radiation at 20 keV.

Figure 34C:
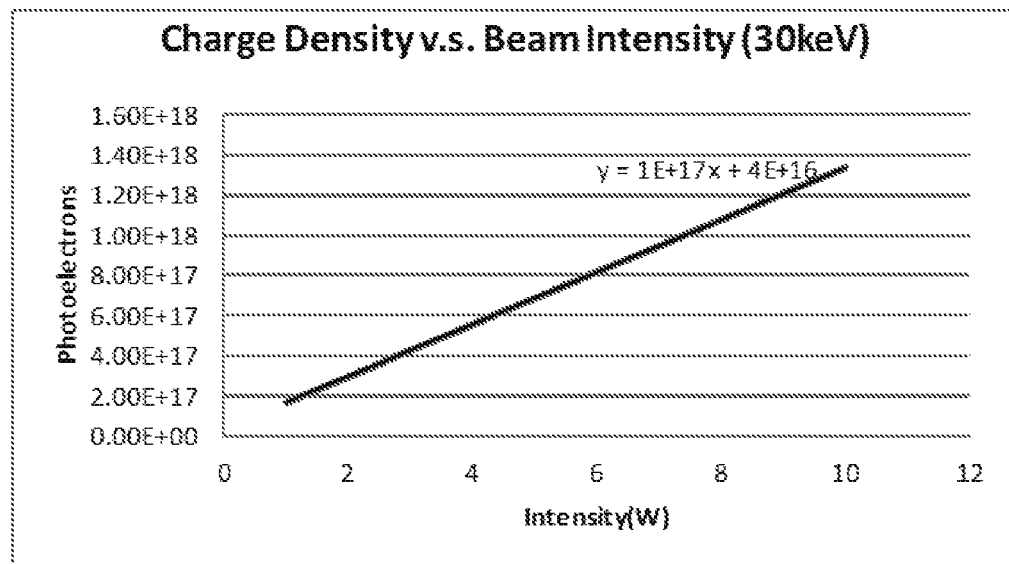

FIG. 34C shows a plot of number of generated photoelectrons versus beam intensity (in W) as a charge response of monochromatic radiation at 30 keV.

Figure 34D:
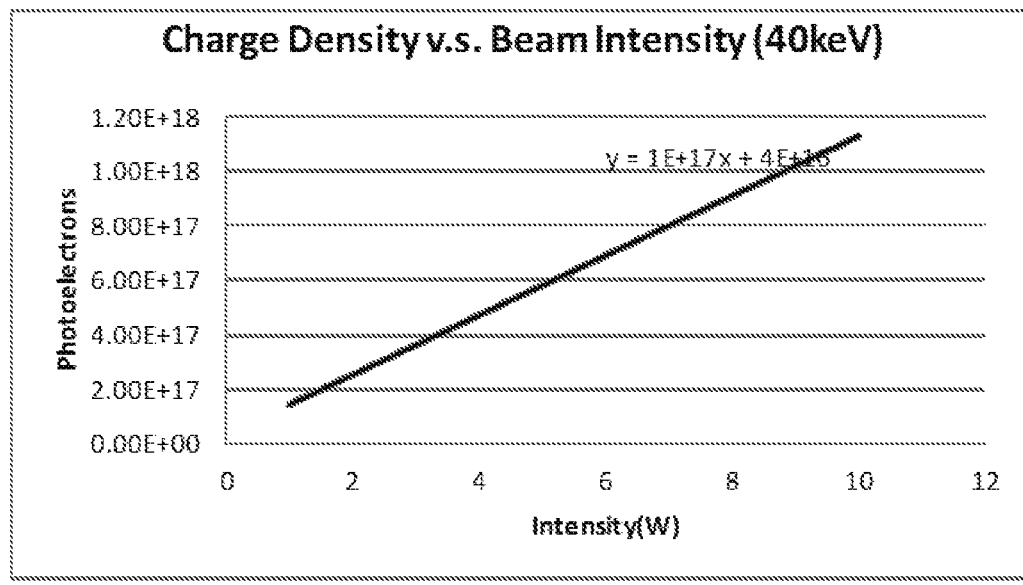

FIG. 34D shows a plot of number of generated photoelectrons versus beam intensity (in W) as a charge response of monochromatic radiation at 40 keV.

Figure 34E:
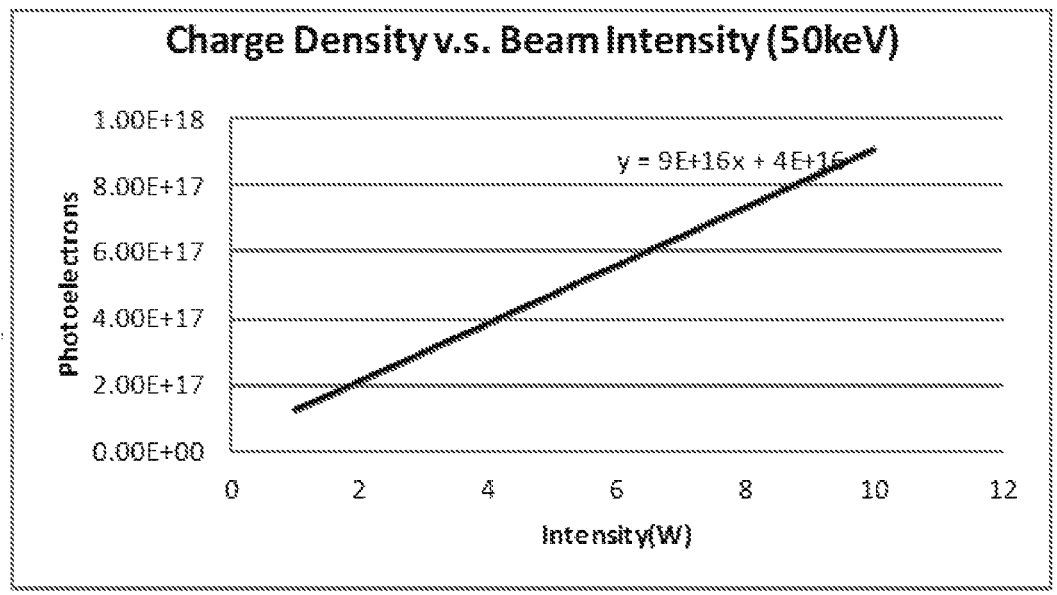

FIG. 34E shows a plot of number of generated photoelectrons versus beam intensity (in W) as a charge response of monochromatic radiation at 50 keV.

Figure 34F:
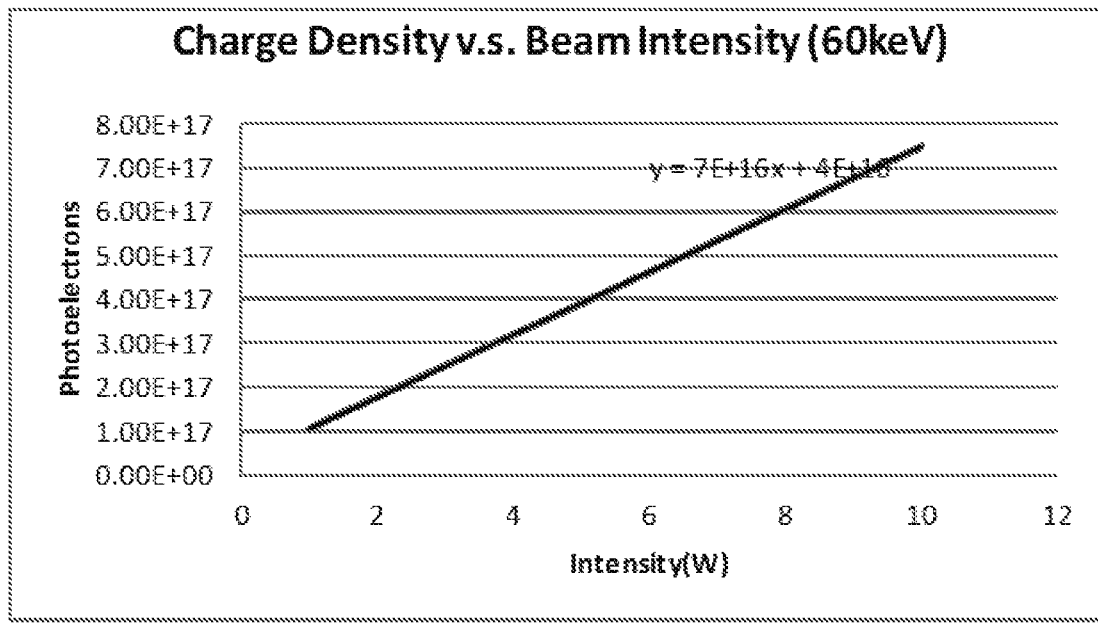

FIG. 34F shows a plot of number of generated photoelectrons versus beam intensity (in W) as a charge response of monochromatic radiation at 60 keV.

Figure 34G:
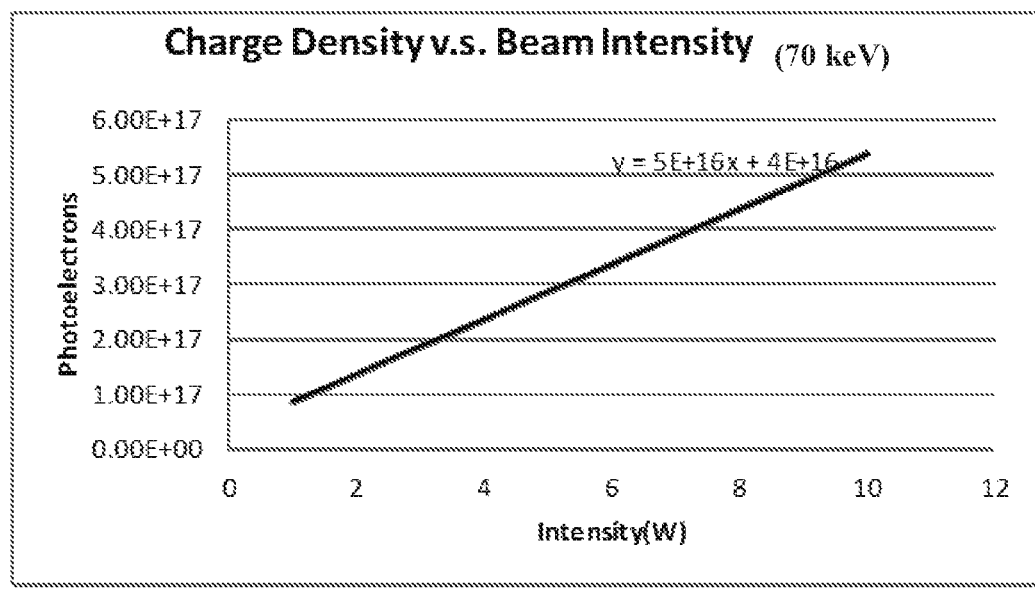

FIG. 34G shows a plot of number of generated photoelectrons versus beam intensity (in W) as a charge response of monochromatic radiation at 90 keV.

Figure 34H:
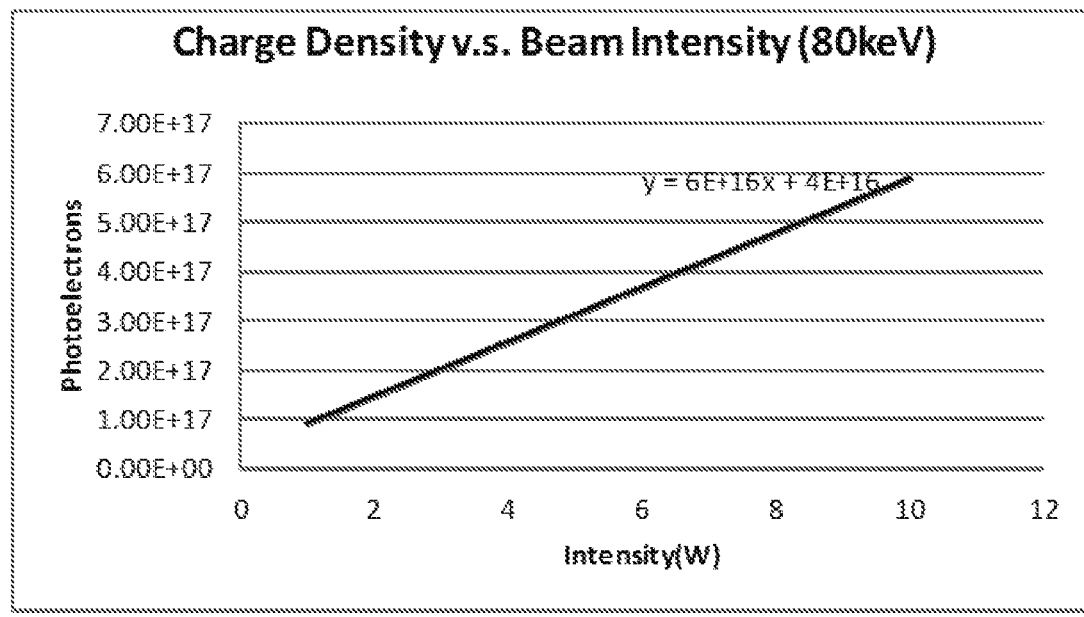

FIG. 34H shows a plot of number of generated photoelectrons versus beam intensity (in W) as a charge response of monochromatic radiation at 80 keV.

Figure 34I:
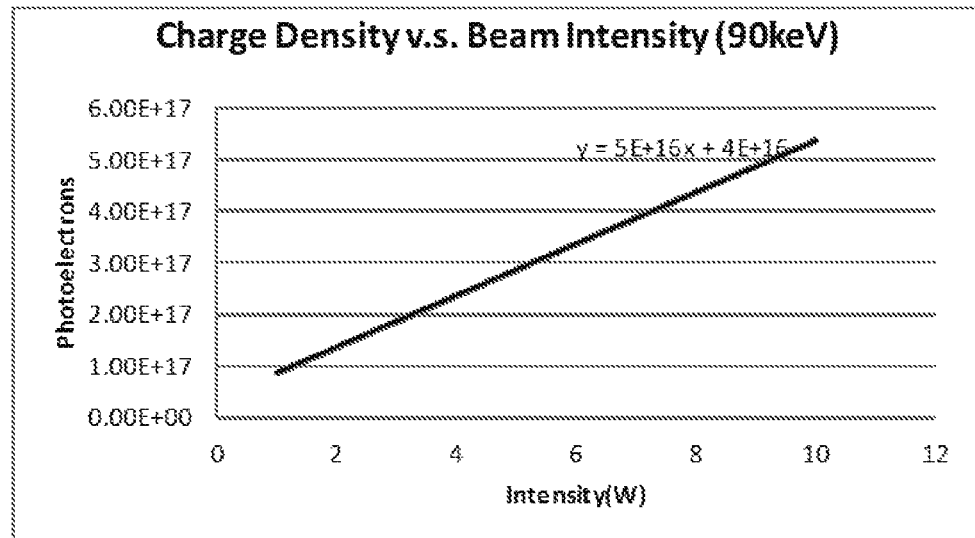

FIG. 34I shows a plot of number of generated photoelectrons versus beam intensity (in W) as a charge response of monochromatic radiation at 90 keV.

Figure 34J:
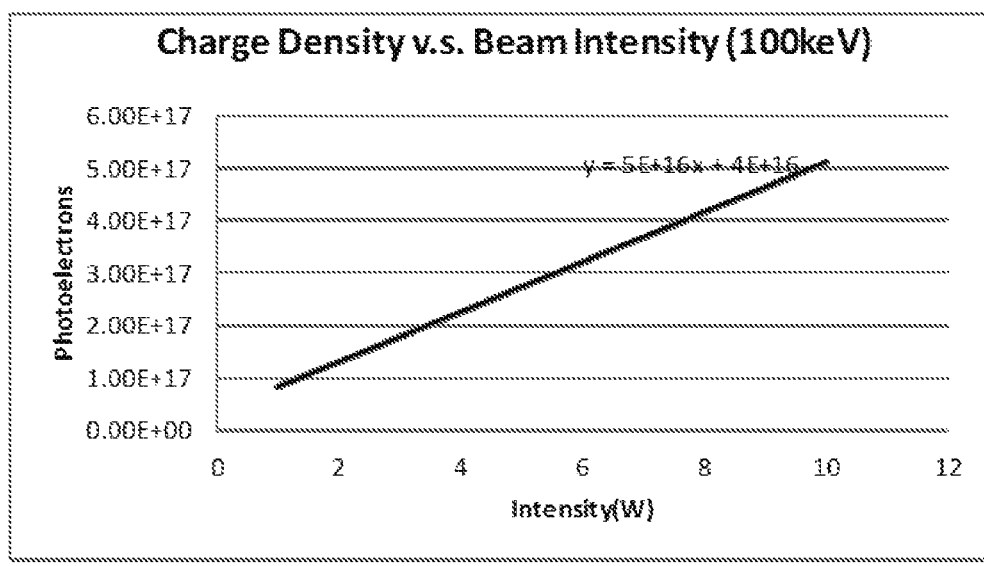

FIG. 34J shows a plot of number of generated photoelectrons versus beam intensity (in W) as a charge response of monochromatic radiation at 100 keV.

Figure 35:
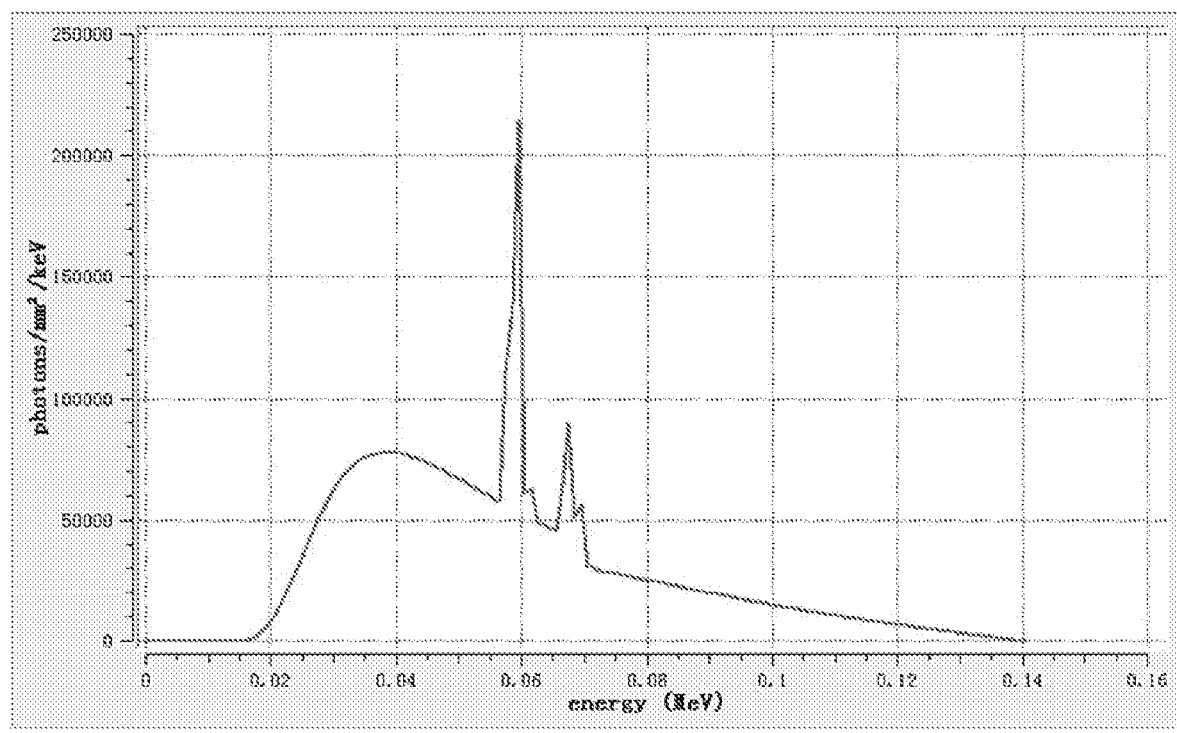

FIG. 35 shows a plot of energy distribution of photons/mm$^2$/keV versus energy in MeV for a generator tube.

Figure 36:
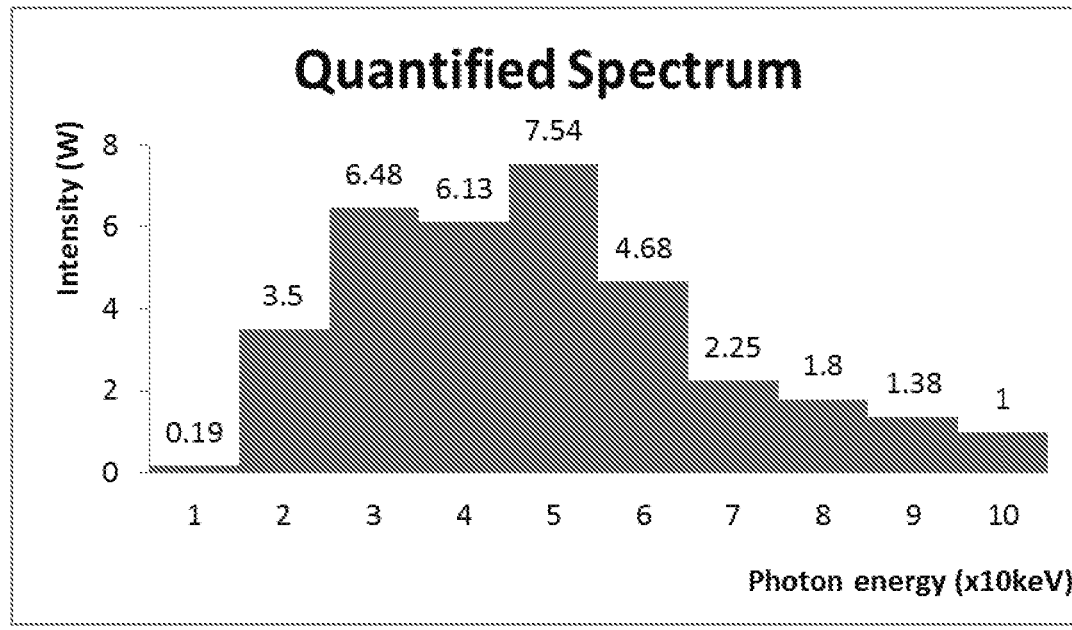

FIG. 36 shows a plot of intensity (W) versus photon energy (×10 keV) as a quantified spectrum.

Figure 37:
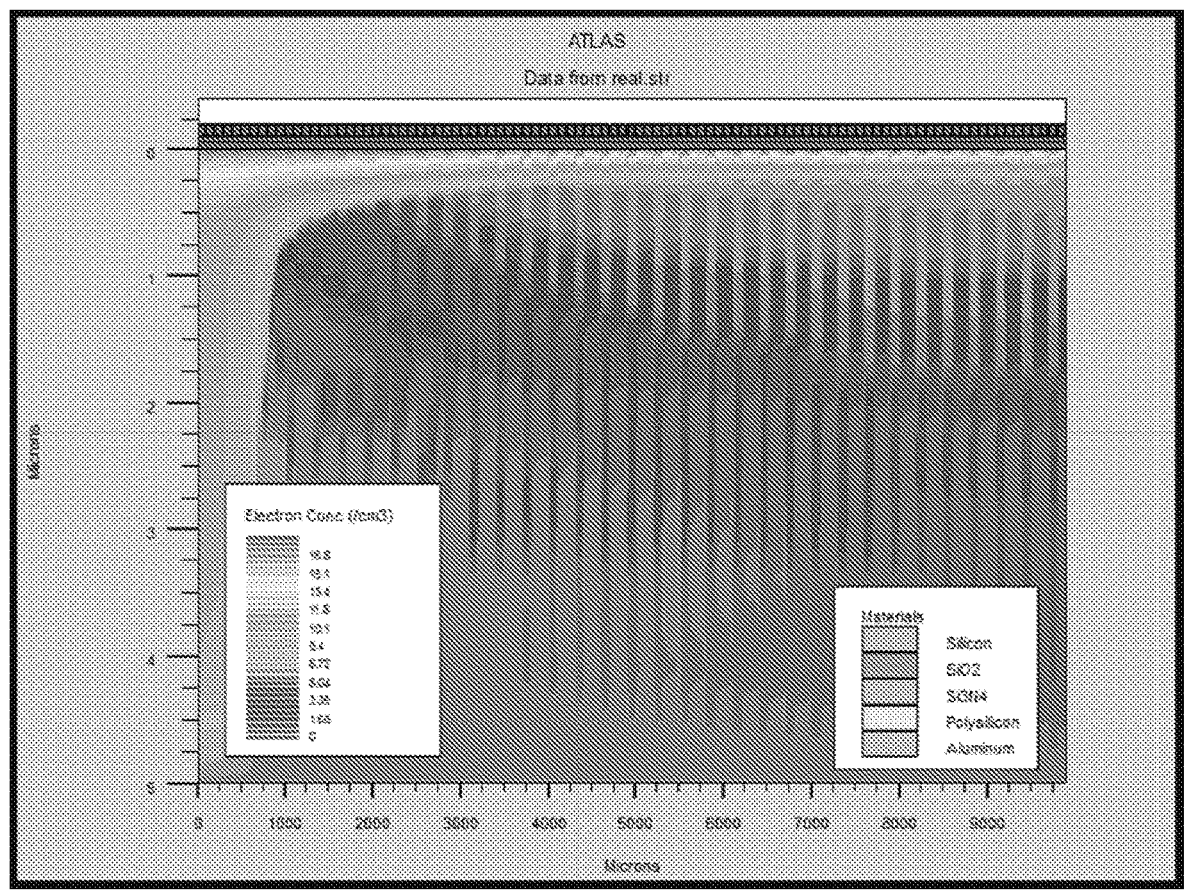

FIG. 37 shows a simulation image of a charged substrate in which photoelectrons are collected in potential wells (PWs). Dividing layers may not be optimized, and four discrete energies of 20 keV, 40 keV, 60 keV, and 80 keV were solved, so the data of four layers can be used to solve the corresponding energy distribution.

Figure 38:
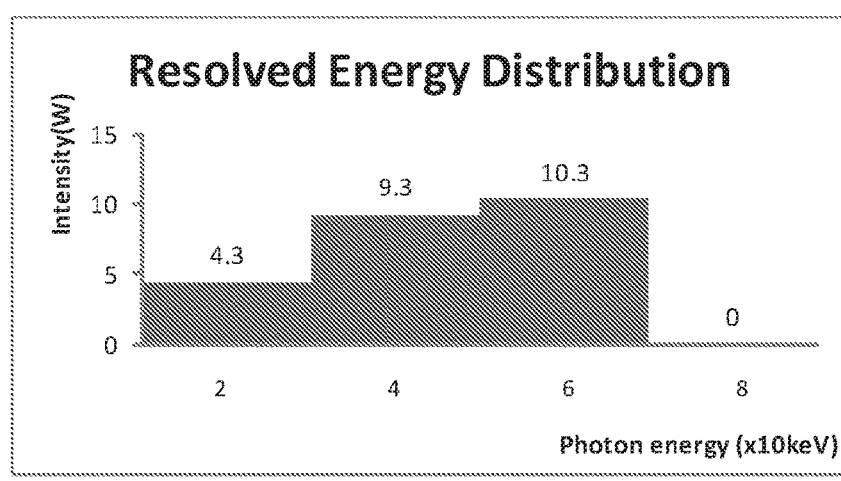

FIG. 38 shows a plot of intensity (W) versus photon energy (×10 keV) as the resolved energy distribution for FIG. 37.

Figure 39A:
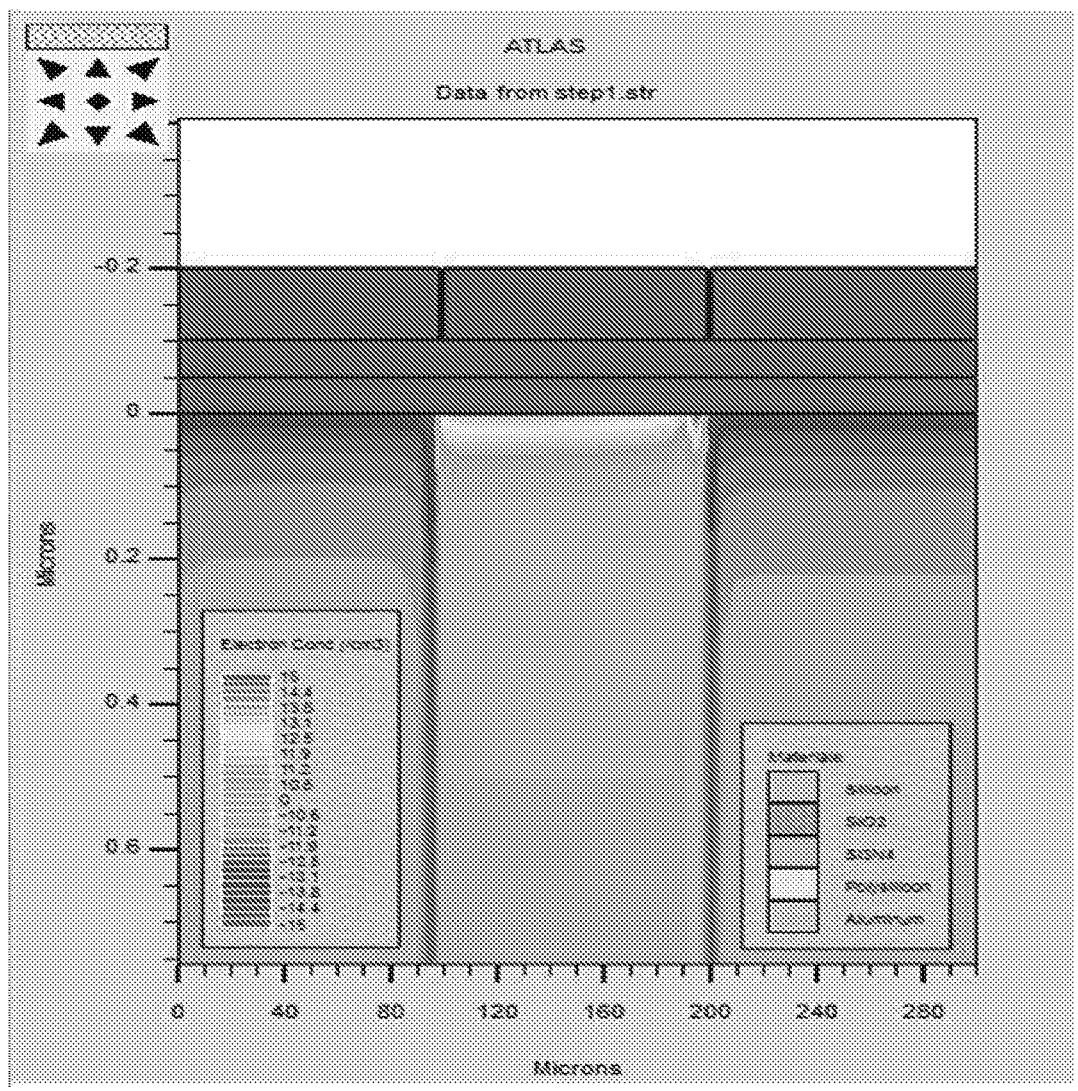

FIG. 39A shows a simulation image of charge transfer between adjacent electrodes.

Figure 39B:
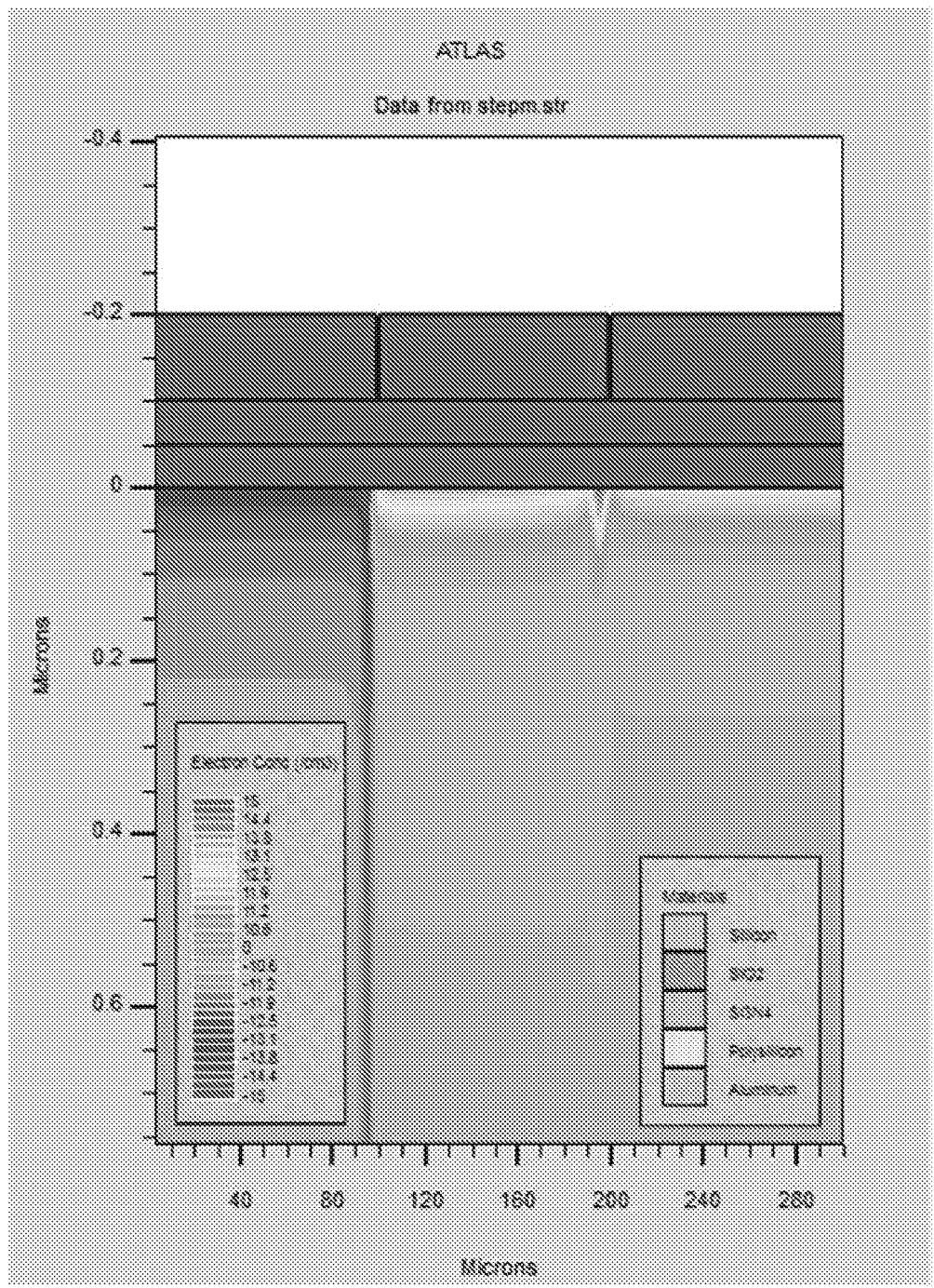

FIG. 39B shows a simulation image of charge transfer between adjacent electrodes.

Figure 39C:
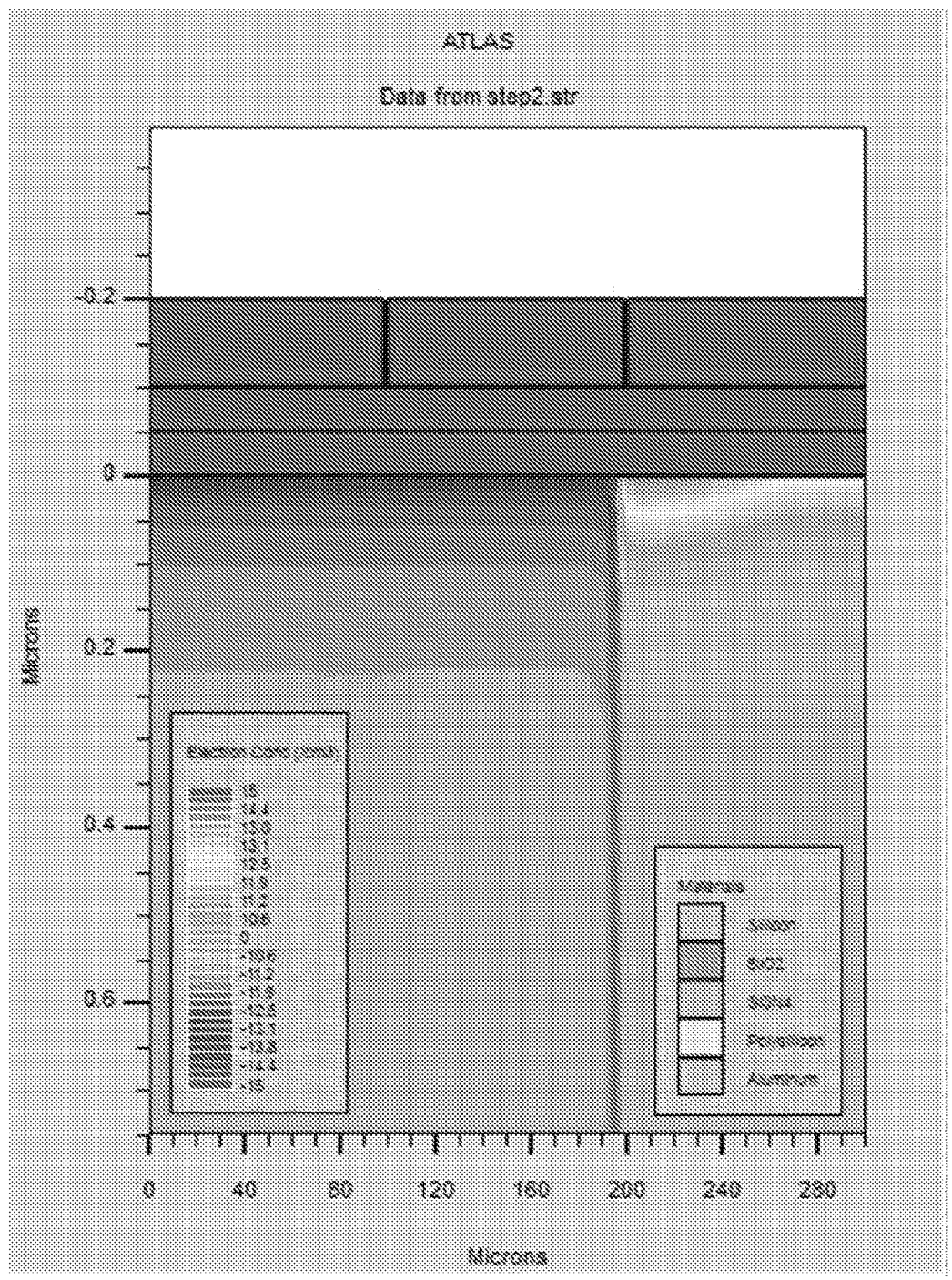

FIG. 39C shows a simulation image of charge transfer between adjacent electrodes.

DETAILED DISCLOSURE

The subject invention provides novel and advantageous methods and systems for performing imaging, such as spectral computed tomography imaging. An edge-on detector, such as a silicon strip detector, can be used to receive X-rays after passing through a sample to be imaged. An energy resolving process can be performed on the collected charges of the collected X-ray radiation. The CT scanner can have third-generation or fourth-generation geometry.

Figures 1A, 1B, 1C:
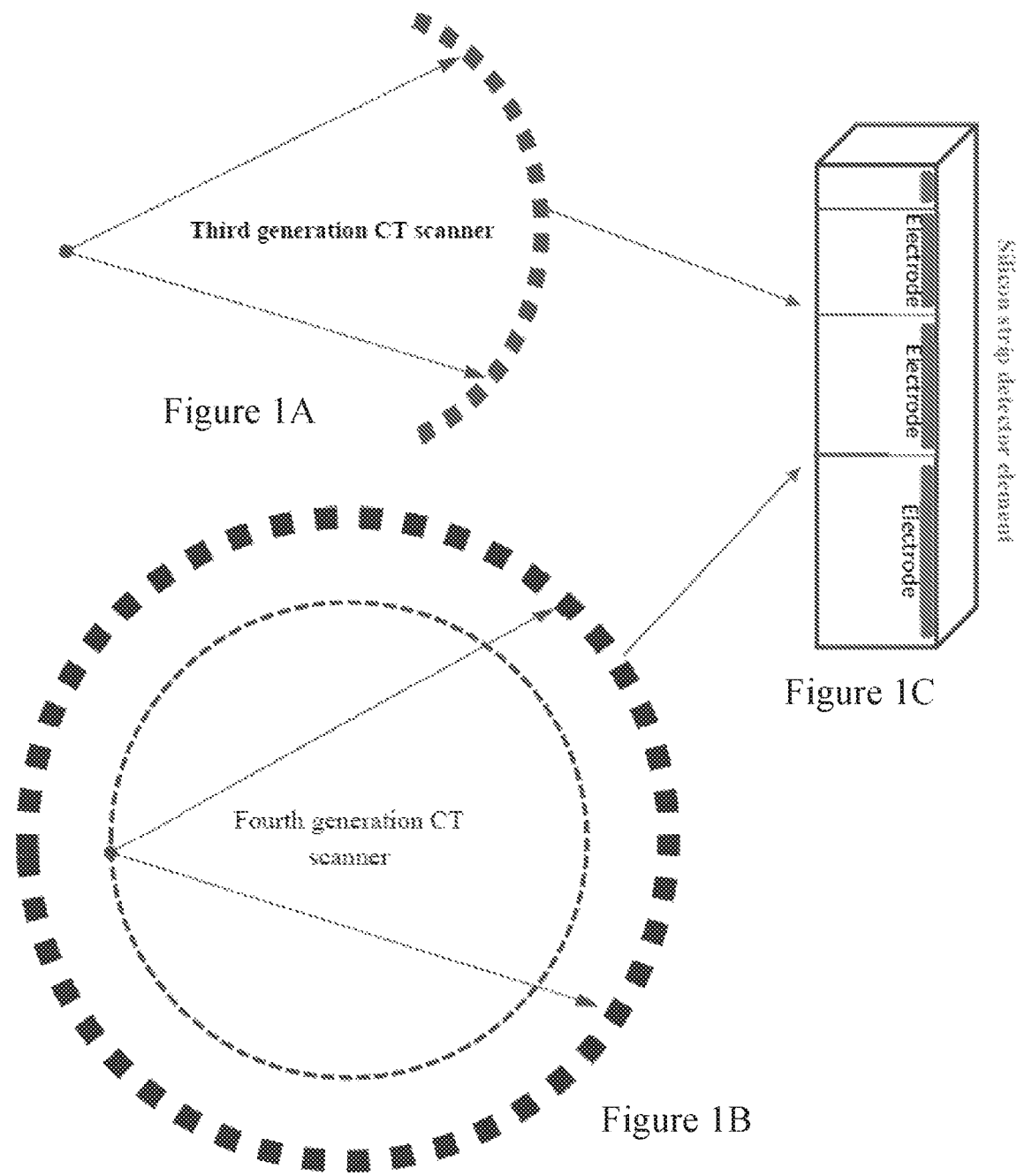
FIG. 1A shows a schematic view of a third-generation spectral computed tomography (SCT) scanner.
FIG. 1B shows a schematic view of a fourth-generation SCT scanner.
FIG. 1C shows a schematic view of a silicon strip detector element for an SCT scanner.
Figure 2:
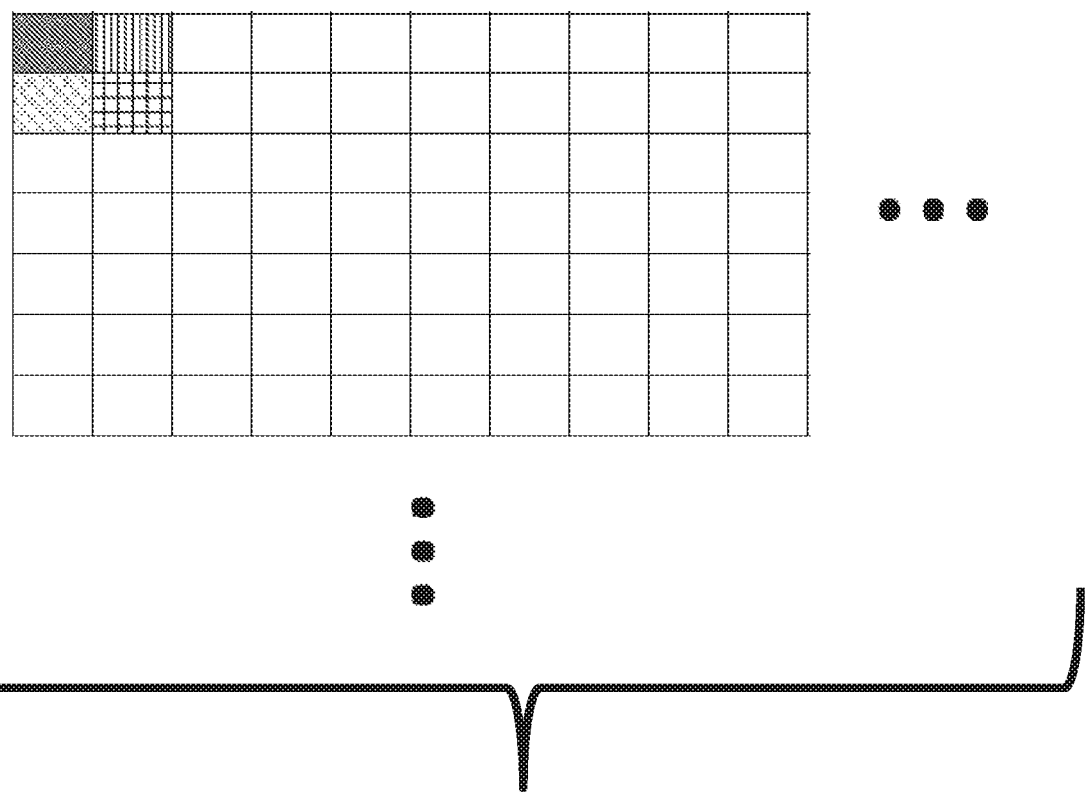
FIG. 2 shows a representative view of a fixed random-thresholding detector.
Figure 3:
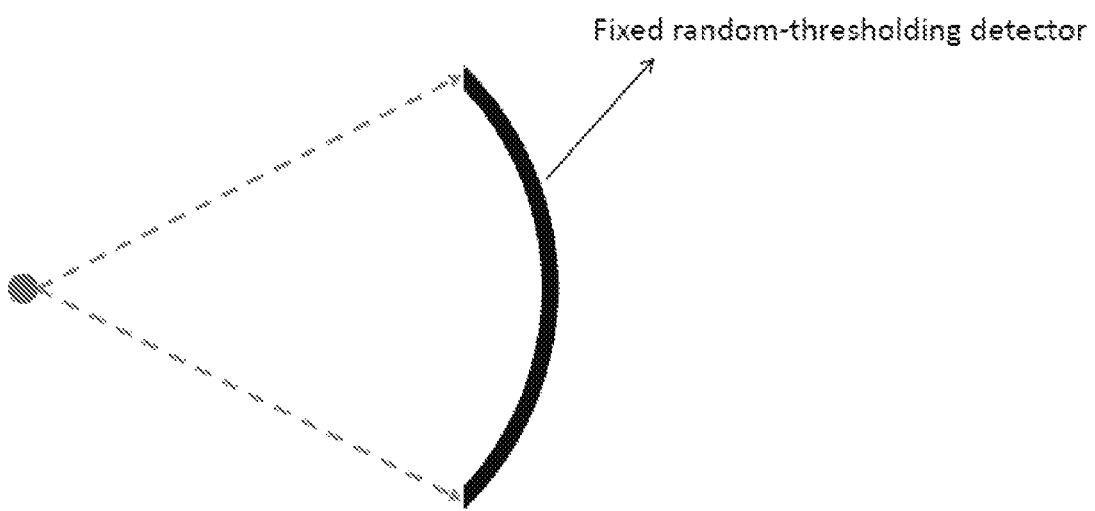
FIG. 3 shows a schematic view of a fixed random-thresholding detector with a third-generation SCT scanner.
Figure 4:
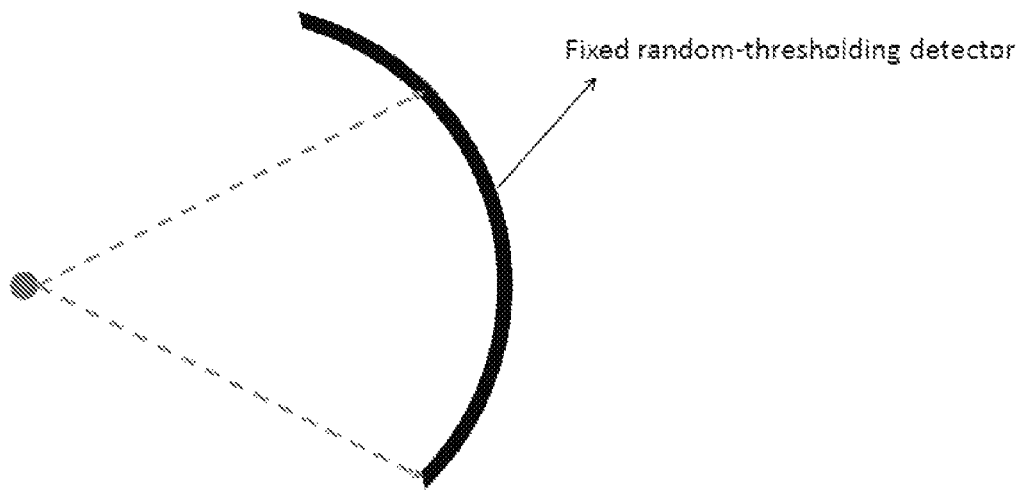
FIG. 4 shows a schematic view of a fixed random-thresholding detector with two slip rings at different speeds. The X-ray tube and detector array can be located on different slip rings, which can be set at different speeds.
Figure 5:
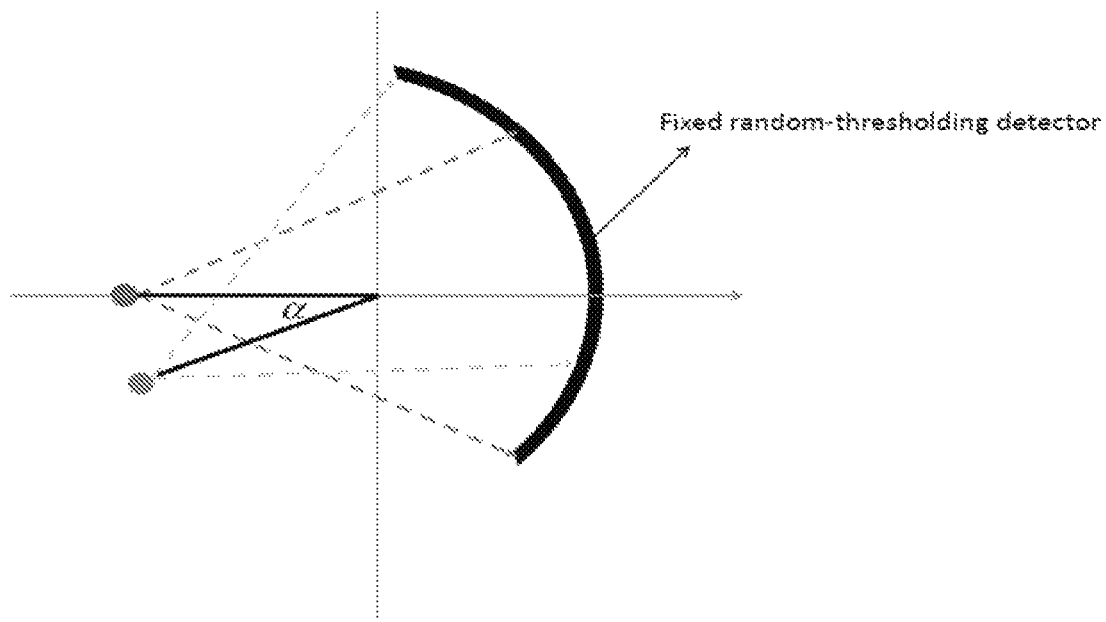

Embodiments of the subject invention can include and/or be used with spectral CT architectures in the third-generation or fourth-generation geometry. The spectral-sensing detector can be used in a spatially-fixed threshold or dynamically-changing threshold. The detector can include but is not limited to a strip-based sensor material, such a semiconductor strip-based sensor material (e.g., a silicon-strip-based sensor material). FIGS. 1-24 show views of third- and fourth-generation geometry scanners and parts thereof. Fixed and changing threshold detectors are depicted in various figures. FIG. 1A shows a schematic view of a third-generation spectral computed tomography (SCT) scanner, FIG. 1B shows a schematic view of a fourth-generation SCT scanner, and FIG. 1C shows a schematic view of a silicon strip detector element for an SCT scanner. FIG. 2 shows a representative view of a fixed random-thresholding detector, and FIG. 3 shows a schematic view of a fixed random-thresholding detector with a third-generation SCT scanner. FIG. 4 shows a schematic view of a fixed random-thresholding detector with two slip rings at different speeds. The X-ray tube and detector array can be located on different slip rings, which can be set at different speeds. FIG. 5 shows a schematic view of a fixed random-thresholding detector with two slip rings at different speeds. If the X-ray tube slip ring speed is X1 Hz, and the X-ray detector slip ring speed is X2 Hz, with X1>X2 or X1<X2, then the maximum turn number N can be determined from:

$$\frac{(N + \alpha/2\pi)}{X1} = \frac{N}{X2}.$$

FIG. 6 shows a schematic view of a fixed random-thresholding detector with two slip rings at different speeds, and also with a sparsely distributed photon counting detector. FIG. 7 shows a representative view of a current integrating detector and photon counting detector, and FIG. 8 shows a schematic view of a fixed random-thresholding detector with a fourth-generation SCT scanner, including a fixed detector array and a half ring. FIG. 9 shows a schematic view of a fixed random-thresholding detector with a fourth-generation SCT scanner, including a fixed detector array, a half ring, and a sparsely distributed photon counting detector. FIG. 10 shows a schematic view of a sparsely distributed random-thresholding detector, with a third-generation SCT scanner, along a full ring.

FIG. 11 shows a top view of a single X-ray source and detector geometry, FIG. 12 shows a side view and sectional view of third-generation CT geometry, and FIG. 13 shows a side view and sectional view of third-generation CT geometry with two slip rings at different speeds. FIG. 14 shows a side view and sectional view of third-generation CT geometry with two slip rings at different speeds, FIG. 15 shows a top view of dual X-ray sources and detector geometry, FIG. 16 shows a top view of triple X-ray sources and detector geometry, FIG. 17A shows a schematic view of a fill ring detector ring design, and FIG. 17B shows a schematic view of a half ring detector ring design.

Each of FIGS. 18-21 shows a schematic view of a current-integrating and photon-counting detector combination. FIG. 22A shows a schematic view of a single-beam pre-collimator design, FIG. 22B shows a schematic view of a multiple-beam pre-collimator design, FIG. 23A shows a schematic view of a design with no post-collimator, and FIG. 23B shows a schematic view of a post-collimator design. FIG. 24 shows a schematic view of a software and hardware method for detection. Only part of the detector ring and one narrow X-ray beam can be shown, if desired.

Photon-counting detectors have advantages over energy integrating detectors, but there are also some disadvantages in the photon-counting mode; namely, slower speed and higher cost. In some embodiments of the subjection invention, a spectral sensing detector design, which is between the energy-integrating and photon-counting schemes, can be used. This can be referred to as "layered energy-integrating" or "grouped photon-counting" so that the two detection extremes are optimally combined with spatially different and/or temporarily changing energy thresholds in the third and/or fourth generation geometry.

A photon-counting detector can sometimes work in 5-8 energy windows, but according to certain embodiments of the subject invention, a spectral sensing detector can work in a lower number of energy windows (e.g., less than 5). The threshold setting can be varied from detector element to detector element but can be fixed during a CT scan. In some embodiments, the threshold setting for each detector can be dynamically changed during a CT scan. The detector elements in either of these cases can be distributed along a full or partial circle or another trajectory (see, e.g., FIGS. 17A and 17B). Image reconstruction can be performed using, for example, a compressive sensing/low-rank pursue/structural coupling scheme, and scattering can be suppressed using scattering suppression methods described herein. The detector (e.g., silicon strip detector) can work through layers to measure X-ray photon energy and intensity. For each layer, energy-integrating and/or photon-counting detection can be used with a layered detecting structure in the energy-integrating mode, thereby resulting in cost-effectiveness and high speed. The X-ray energy information can be extracted according to the penetration depth of the X-ray into the detector (e.g., the silicon strip detector). This type of X-ray detector is easy to fabricate at low cost.

Embodiments of the subject invention can include inhomogeneous arrangement of energy thresholds for individual detector elements, as well as new and advantageous associated detector designs, image reconstruction methods, and scatter correction methods. The scatter correction and the image reconstruction can be interrelated and iteratively performed. The use of a silicon strip detector in the third-generation or fourth-generation geometry is an advantageous framework for spectral CT. Embodiments of the subject invention including and/or used with fourth generation geometry with fixed detector thresholds or third generation geometry with dynamic detector thresholds can operate more effectively than related art spectral CT detectors, including those that use high-density expensive materials.

While conventional computed tomography (CT) is based on energy integrating detectors for the acquisition of X-ray photons, spectral CT offers more clinical information for disease diagnosis, including discrimination of tissues, differentiation of calcium and iodine, and detection of smaller vessels. Spectral CT can also reduce beam hardening artifacts and metal artifacts. Some embodiments of the subject invention include integrating a detector, such as a strip detector (e.g., a silicon strip detector) with certain geometries of detectors (e.g., third-generation and/or fourth-generation geometry). A strip detector (e.g., a silicon strip detector) can use layer mode to acquire X-ray photon energy information. For each layer, energy integrating detection can be used for the acquisition of the X-ray photons. The X-ray energy information can be quantified according to the depth of penetration of the X-ray into the silicon strip detector (e.g., silicon strip detector). Such an X-ray spectral detector is easy to fabricate with low cost and can have many useful applications, including but not limited to medical imaging.

Spectral detectors extract photon energy information, and a semiconductor strip detector can use the depth information of penetration of an X-ray into the semiconductor strip detector to discriminate the energy of X-ray photons. FIG. 27 shows a schematic view of an X-ray detector. Referring to FIG. 27, the detector can be a semiconductor strip detector (e.g., a silicon strip detector) and can include multiple layers (depending on the number of energy bins). The layers can have varying heights to achieve an approximately uniform number of photons in each layer. Electrical connectors can be connected to every layer of the strip detector to sense the current signal. The energy of each interacting X-ray can be quantified based on the depth of penetration of the X-ray into the detector. To discriminate X-ray photon energy, an incident X-ray beam of a given energy and unit intensity for an appropriate counting interval can result in a set of numbers. $N_i$, reflecting the photon number in layer i, where the index i refers to the number of a layer. Repeating this process for different X-ray energies will yield the element Mij of point spread function matrix. Letting Sj represent the incident energy spectrum after traversing an absorber, the counts observed can be given by $$C=[M_{ij}]S \qquad (1)$$

M can be generated for a given system by theoretical calculations using the geometry of the detector, attenuation data of the material (e.g., silicon), and the X-ray source energy spectrum. Once the matrix is generated, the solution can be extremely stable. The rapid variation of the attenuation length with energy can ensure that the inverse of M is well-behaved. Once M is inverted, X-ray spectral information can be extracted:

$$E=M^{-1}C \qquad (2)$$

Thus, using the segmented strip detector as depicted in FIG. 27, energy dependent information contained in the vector E can be manipulated to emphasize soft or bony tissues for image presentation. In addition to the matrix approach described herein to extract energy information, other methods also exist for maximizing computational efficiency. Simpler methods, such as least squares fitting to the segment data, also provide a robust technique for the extraction of energy information.

Detector designs for dynamic grouping X-ray sensing layers of the subject invention are flexible, and a cost-effective design that uses fixed thicknesses of X-ray detecting layers can be used, instead of performing dynamic grouping or dynamic thresholding. As far as an individual detector cell is concerned, a detector configuration of fixed layers can be considered a simple extension of a dual-layer detector design, such as that used on the Phillips spectral CT detector. In some embodiments of the subject invention, all involved detector cells can have different relative thicknesses. As a result, each X-ray beam spanned by a detector cell aperture can advantageously sense the entire X-ray spectrum in a different way. For example, in a dual-layer detector design, nine variants of the dual-layer detector can be used, which respectively break the X-ray spectrum from low to high energies into 10% to 90%, 20% to 80%, ..., 90% to 10% parts. In a particular embodiment, these detector variants can be distributed in a natural sequence and repeated until a full detector ring is covered in the fourth generation geometry. Such a detector design can be easily implemented and can be considered as a particular case of detector design. A key is that one or more advanced reconstruction algorithms can be used to recover spectral information in multiple energy bins significantly more than what dual-energy CT could do.

In an embodiment a. silicon layer detector can be integrated with a fourth generation CT scanner to acquire an X-ray spectral signal. The fourth-generation geometry has spectral detectors that are fixedly placed around a patient and an X-ray tube that rotates around the patient, for example as shown in FIG. 8. Spectral detectors can be placed in third-generation geometry, for example as shown in FIGS. 3-6.

When an X-ray beam interacts with an object, some photons may be deflected from the original propagation direction, yielding photon scattering. X-ray scattering can be described by incoherent scattering (Compton scattering) and coherent scattering (Rayleigh scattering). Generally, Compton scattering occurs at high radiation energy, and coherent scattering takes place at lower radiation energy. It can sometimes be more difficult to detect X-rays with low energy (less than 30 keV) when scanning a human body. Thus, when scanning a human body, Compton scattering can be expected to dominate.

Compton scattering describes the ionizing interaction of a photon with a free electron in an outer shell of an atom. A fraction of the X-ray energy can be transferred to the electron, and the electron can be ejected and the X-ray photon lost energy can deflect its propagation direction. The differential scattering cross-section can give the probability of photons being scattered into a given solid angle from a free electron, and can be expressed by the Klein-Nishina formula, $$\frac{d\sigma_{compton}}{d\Omega}(\varphi) = \frac{r_e^2}{2[1+\alpha(1-\cos\varphi)]^2}\left[(1+\cos^2\varphi) + \frac{\alpha^2(1-\cos\varphi)^2}{1+\alpha(1-\cos\varphi)}\right] \quad (3)$$

where $\varphi$ is the scattering angle, $=E_\gamma/m_ec^2$, $E_\gamma$, $E_r$ the photon energy, $m_e$ the electron mass, c the speed of light, and $r_e$ the classical radius of the electron. From the definition of the differential cross-section of photon scattering, the first order X-ray scattering intensity D(r, E) at energy E detected by a detector at a position r can be described as follows:

$$D(r, E) = Ds \cdot I_0 \int \int_V s(r_s)\rho_e(r_s) \frac{d\sigma_{compton}}{d\Omega}(\beta) \frac{n \cdot (r-r_s)}{|r-r_s|^3} \quad (4)$$
$$\exp\left(-\left(\int_{l(r_0,r_s)} \mu(\tau, E)d\tau + \int_{l(r_s,r)} \mu(\tau, E)d\tau\right)\right)dr_s,$$

where $s(r_s)$ is the solid angle which the voxel element v(r) in the object can be covered, Ds is the area of a detector element, n is the norm direction of the detector element, v is the direction of the x-ray beam at energy E that interact with voxel element v(r), $\beta$ is the deflection angle of the photon toward detector element and $$\beta = \cos^{-1}\left(\frac{(r-r_s) \cdot v}{\|r-r_s\|}\right),$$

and $\rho(r_s)$ the electron density at the position $r_z$, $l(r_0,r_s)$ is the path from source position $rl_0$ to voxel element $vl(r_s)$, $l(r_s,r)$ is the path from the voxel element $v(r_s)$ to detector element r. The electron density $\rho(r)$ has a relation with the attenuatin coefficient $\mu(r,E)$ $$\mu(r|, E) = \rho_e(r)\left(15\alpha^4\pi r_e^2 \frac{Z^3}{E^3} + f_{kn}(E)\right), \quad (5)$$

where $\alpha$ is the fine structure constant (~0.0073), $r_e$ is classical radius of the electron ($r_e$=2.818 fm), and Z is the atomic number. The X-ray intensity at energy E measured by a photon counting detector can be described from the Beer-Lambert law, $$I_E - D(r, E) = I_0S(E)\exp\left(-\int_l \mu(\tau, E)d\tau\right), \quad (6)$$

where $I_E$ is the total X-ray intensity measured by a detector, S (E) is the spectrum of the X-ray source, S (E)>0, and m (r,E) is the linear attenuation coefficient at an energy E in a spatial position r along an x-ray beam path l. Equation (6) is the scattering correction equation for the spectral detector. Integrating both sides of Equation (6), a scattering correction for the gray-scale detector can be also obtained.

Equations (3)-(6) are an equation system with an attenuation coefficient. An iterative method can be used for the X-ray spectral CT, and the spectral image reconstruction can be performed by jointly solving Equations (3)-(6).

In the fourth-generation geometry, detectors can be fixedly placed around a patient and an X-ray tube that rotates around the patient. The field of view of the X-ray source, primary X-rays, only covers part of the detector elements. These detector elements out of the field of view of the source can acquire X-ray scattering photons. The intensity of X-ray Compton scattering measured by each detector element can be described from Equation (4), which establishes a linear integral equation with respect to the electron density. When the X-ray tube rotates around the patient, these detectors out of field of source view can measure a scattering signal of the object at each projection view. These measured scattering signals can form a system of linear equations from Equation (4) to reconstruct an electron density distribution of the object. The reconstructed electron density distribution can be applied for Equation (4) for a higher accuracy scattering correction.

SCT is an effective approach to obtain tissue information with high resolution and low contrast-medium density. An X-ray detector is a pivotal component of SCT, and for further imaging, an X-ray detector aims to resolve energy distribution of incident radiation (i.e., the spectrum). Two approaches to transform X-ray energy information into charge signals are direct conversion and indirect conversion. Unlike indirect conversion, which needs an intermediate step to convert radiation into light by a scintillating medium before obtaining a charge signal, SCT directly converts X-ray energy into charge information and achieves higher spatial resolution. The attenuation coefficient of photons increases rapidly when their energy is above the binding energy of k-shell electrons of atoms they are interacting with, and SCT takes advantages of this property, providing more accurate details of soft-tissue.

Energy-resolving is a main component of image reconstruction in SCT. Photon integrating and photon counting detectors (PCD) are two main solutions to resolve incident radiation energy. In a photon integrating approach, charge response to radiation impulse is analyzed as a whole regardless of the energy distribution, and then the average attenuation efficient at that specific point (or pixel) is derived from the pixel value. In fact, attenuation of X-rays varies for different energy/frequency, so much information can be missed in conventional imaging with photon integrating. Photon counting can be used to resolve energy distribution in SCT and can use a silicon strip detector. With photon counting, the detector theoretically can obtain detailed photon energy and counts, and it is capable of detecting several kinds of human body tissue if energy thresholds are set properly. If an appropriate material and readout device are applied, photon counting can provide higher signal-to-noise ratio (SNR) in comparison with a traditional photon integrating approach. Thus, photon counting to some extent takes advantage of low energy information of X-rays, and is able to provide higher resolution. One drawback of photon counting is that accurate control is required to decide whether the impulse is generated by one photon with high energy or several photons with lower frequency (known as pile up), and this puts more pressure on the photon counting detector to provide a satisfactory detecting rate.

As a beam of X-rays injects into a photoconductor substrate, photons interact with local atoms and electrons, photon annihilation and electron generation can occur. Cadmium telluride (CdTe) and cadmium zinc telluride (CTZ) can be used as energy-resolving pulse detectors in certain embodiments of the subject invention, and these materials have high assimilating efficiency for X-rays with high energies because of their high-z (high atomic number) property. It can take a long time for CdTe/CTZ materials to collect and transfer charge response since these materials have a relatively low charge mobility. Therefore CdTe and CTZ detectors are more likely to suffer from a pile up problem. Moreover, CdTe and CTZ have higher manufacturing cost in comparison with silicon, which also has satisfied electron mobility to work at a high rate. On the other hand, silicon has a low atomic number, and therefore X-ray degrades in silicon materials slowly. To fully assimilate an X-ray beam, a silicon sensor must be very thick.

The interaction scheme between photons and atoms when X-rays travel in materials with a low atomic number will now be discussed. Photoelectric effect and Compton scattering are two main mechanisms of photon absorption. During photoelectric effect, one photon is annihilated along with the generation of one electron. In this case, generated charge density represents the photon density. Because photon absorption is depth and energy dependent, photon energy distribution can be obtained from generated charge density at different positions. However, because silicon has a relatively low atomic number, Compton scattering is more likely to happen when an X-ray with an energy over 40 keV, travels through the silicon bulk. When a Compton effect occurs, one photon is usually able to generate several electrons and this uncertainty makes it more difficult to determine the correct charge generation effect and can therefore cause distortion of the final data in certain instances.

As charge information needs to be read out for post-processing, charge coupling is a competent approach to transfer collected charge information out. Mature silicon fabrication technology and successful CCD (charge coupled device) structures allow this technology to be applied to X-ray detection and CT. Conventional CCD can be used for visible light detection, and typically involves accepting light from its gate side or substrate side and transferring the beam signal into a charge signal, which can then be read out by corresponding readout circuits. When an X-ray travels through a silicon-based CCD, in some cases only a small fraction of the incident X-ray, which has a relatively low energy, can be assimilated by the bulk because of the low atomic number of silicon. Although a CCD can be used to detect soft X-rays by altering the material resistance and dielectric, it can still be difficult for general CCD devices to handle high energy x-rays, which can travel in silicon materials for centimeters before being fully absorbed. In some embodiments of the subject invention, an edge-on structure can be used to detect an X-ray beam with a wide range of energy distribution.

To address concerns of related art devices and methods, some embodiments of the subject invention include energy-resolving models and devices for spectral CT, which can include an edge-on structure detector. In the design, X-rays can enter the silicon bulk from one side, interact with atoms, and generate electrons that can be collected in potential wells (PWs). The collected charge can be transferred consecutively along the incident direction to a readout circuit and then be digitalized.

When an X-ray travels inside silicon bulk, photons can interact with local atoms and generate electrons. A general expression of photon degradation in semiconductors is shown in Equation (7).

$$G = \eta_0 \frac{P\lambda}{hc} \alpha e^{-\alpha y} \qquad (7)$$

where P is the X-ray intensity factor containing cumulative effects of reflections, transmissions, and absorption over ray path, $\eta_0$ is the internal quantum efficiency which indicates the amount of carrier pairs generated per photon, h is Planck's constant, c is the speed of light, and $\alpha$ is the mass attenuation coefficient. The mass attenuation coefficient varies as photon energy changes and can be found published on the National Institute of Standards and Technology website.

X-rays used for body tissue and bones can have a wavelength in a range of from 0.01 nm to 0.06 nm, and can correspond to an energy of from 0.01 MeV to 0.1 MeV. In this case, there are two main mechanisms of photons being degraded: (1) Electro-photon (EP) effect (or photoelectric effect) and (2) Compton Scattering. In the EP effect, electrons within semiconductor materials can absorb energy of an incident beam. If the energy is greater than the band gap energy of the semiconductor, an electron is then able to jump to the conduction band and become a free electron. In the EP scheme, generation of charge follows an "All or Nothing" principle in that one photon is annihilated and its energy is used to generate one electron and its kinetic energy. However, a large fraction of high energy photons can be scattered in silicon, and the Compton Effect can lead to great uncertainty. Thus, a more accurate model of photon-atom interaction is advantageous.

Photon absorption in semiconductors is energy and position dependent. For simplicity, Equation (7) can be reduced to the following form.

$$\begin{cases} R = 0.090 \rho^{-0.8} E^{1.3} & \text{for } E < 10 \text{ keV} \\ R = 0.045 \rho^{-0.9} E^{1.7} & \text{for } E > 10 \text{ keV} \end{cases} \quad (8)$$

where E is incident beam energy, R represents the thickness needed to fully assimilate incident beam at energy E, and $\rho$ is material density. Equation (8) provides a solution to resolve incident beam spectrum. For a silicon substrate, particularly, the Fano factor can be quite small, which can indicate that most of the degraded energy contributes to charge generation. Thus, generated charge density can be represented by Equation (9).

$$N \approx \frac{E}{E_0} \quad (9)$$

where E is X-ray energy and $E_0$ is energy needed to generate one electron, which is usually related to material band gap. Equation (9) also indicates that generated electron density is proportional to the photon energy/frequency, so the linear features discussed herein can be sued to provide an approach to solve for the incident spectrum.

Photon attenuation is related to material, frequency, and thickness. Usually, X-rays used in CT contain various energy components ranging from, for example, 20 keV to 120 keV, and X-ray degradation in semiconductors can follow a certain process. When the X-rays travel through silicon material with a fixed thickness, photons can be absorbed at different levels depending on the frequency. At the same time, electrons can be generated with the absorption of photons. This procedure can be summarized in Equation (10).

$$m_1 E_1 N_1 a_{k1} + m_2 E_2 N_2 a_{k2} + \ldots + m_n E_n N_n a_{kn} = g_k(x) \quad (10)$$

where $E_i$ denotes different photon energy, $N_i$ is photon density with energy $E_i$, $a_{ki}$ is the attenuation coefficient of photon with energy $E_i$ for the given material thickness, and $m_i$ is an empirical coefficient that represents the number of generated charge by photons with energy $E_i$ per energy unit. Therefore, $g_k(x)$ is generated charge density within the silicon bulk with a specific thickness. Equation (10) is reasonable under the linear approximation (Equation (9)), and the assumption that composite X-rays can be regarded as a linear combination of monochromatic radiations is valid. In an embodiment of the subject invention, to solve energy distribution, $N_i$ can be obtained in Equation (10). The more equations obtained, the more accurate the energy spectrum will be. Therefore, if the same X-ray source is applied on the same material to obtain charge information within different thicknesses (or layers), the equation can be solved to obtain as many energy components possible. In addition, $E_i$, $a_{ki}$, and $m_i$ can be obtained if the material and its thickness are defined. Therefore, an important factor is deriving the amount of generated charges.

The energy resolving method of the subject invention provides certain advantages. For example, because required thickness to fully absorb an X-ray beam varies for radiations with different frequencies, layer thickness can be dynamically changed in a post-processing stage to accommodate the X-ray source and achieve maximum precision and minimize system error.

FIG. 30 shows a schematic view of an edge-on photon absorption scheme and device according to an embodiment of the subject invention. Referring to FIG. 30, the design is similar to a metal-oxide-semiconductor (MOS) structure, but the bulk is far longer than that of a MOS structure because X-ray can travel a long distance inside silicon. In this design, an X-ray beam enters the substrate from one side. As it travels inside the silicon substrate, photons will interact with local atoms and generate electrons. If proper bias is applied on the metal electrodes, generated charges will be collected in PWs. Along the direction of the incident beam, a summation of the amount of charges in the first several PWs provides one constraint of Equation (10). Changing the number of PWs taken into account results in obtaining multiple equations (i.e., multiple versions of Equation (10)) corresponding to different thicknesses, thereby allowing for the energy distribution to be solved for.

The charges can be quantified, for example, by an analog-to-digital convertor (ADC). Before the collected charges can be quantified by an ADC, though, they should be transferred from the substrate to an adjacent readout circuit. For example, the same charge transfer approach as a CCD uses can be used here. As long as proper biases are applied on the electrodes, collected charges can move into its neighbor PW. FIG. 31 shows a 3-phase charge transfer model that can be used in an embodiment of the subject invention.

Referring to FIG. 31, at time t1, only v1 is set high, so generated charge can be collected in the PW during exposure; at t=t2, both v1 and v2 are biased at a high level, when there is no barrier under the two gates, collected electrons can then flow to the PW under electrode v2; then, at t=t3, only v2 is biased at a high level, and under this condition, all the electrons are transferred to the adjacent electrodes. This procedure can be repeated, such that collected charge under each gate can be transferred to the right-most readout circuit.

As X-rays pass through human body, they gather important body tissue information. SCT technologies can provide high quality images of human body tissue by analyzing all information (e.g., the spectrum). However, because of material constrains, it can be difficult to obtain the beam spectrum precisely with existing technologies, so a large fraction of energy information may be ignored. Although photon-counting technology, which obtains photon energy information by detecting photocurrent pulse, can achieve higher resolution, it requires more accurate control logic and faster readout speed. In many embodiments of the subject invention, alternative approaches to resolve energy distribution can be used. An X-ray assimilation scheme can be used in a material (e.g., a semiconductor material such as silicon, though embodiments are not limited thereto) and can be based on an energy resolving model together with linear approximation of photon absorption. An edge-on structure can be used with and/or correspond to the energy resolving model. In such a structure, the photon-generated charge can be transferred out sequentially in a device similar to a CCD. As shown in the examples presented herein, the methods and devices described herein are functional and valid, can obtain the radiation spectrum from a CT scan, and can drastically improve CT resolution.

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The subject invention includes, but is not limited to, the following exemplified embodiments.

Embodiment 1. A method of imaging, comprising:
providing X-ray radiation to a sample to be imaged;
collecting the X-ray radiation with a detector; and
performing an energy resolving process on the collected X-ray radiation (e.g., on collected charges of the X-ray radiation).

Embodiment 2. The method according to embodiment 1, wherein the energy resolving process includes:
determining the generated charge density within the detector using Formula 1:

$$m_1 E_1 N_1 a_{k1} + m_2 E_2 N_2 a_{k2} + \ldots + m_n E_n N_n a_{kn} = g_k(x) \quad \text{Formula 1}$$

where $E_i$ is photon energy, $N_i$ is photon density with energy $E_i$, $a_{ki}$ is the attenuation coefficient of photon with energy $E_i$ for the given material thickness, $m_i$ is an empirical coefficient that represents the number of generated charges by photons with energy $E_i$ per energy unit, and $g_k(x)$ is the generated charge density within the material of the detector of a specific thickness; and
repeating the determination of the generated charge density at a different thickness within the material of the detector.

Embodiment 3. The method according to any of embodiments 1-2, wherein the detector is a strip detector.

Embodiment 4. The method according to any of embodiments 1-3, wherein the detector is a semiconductor strip detector.

Embodiment 5. The method according to embodiment 4, wherein the semiconductor is silicon such that the detector is a silicon strip detector.

Embodiment 6. The method according to embodiment 4, wherein the semiconductor is cadmium telluride (CdTe).

Embodiment 7. The method according to embodiment 4, wherein the semiconductor is cadmium zinc telluride (CTZ).

Embodiment 8. The method according to embodiment 4, wherein the semiconductor is silicon, CdTe, or CTZ.

Embodiment 9. The method according to embodiment 5, wherein a bulk material of the silicon is $p^-$ silicon.

Embodiment 10. The method according to any of embodiments 1-9, wherein the detector includes a plurality of potential wells.

Embodiment 11. The method according to any of embodiments 1-10, wherein the detector has a structure that mirrors that of a MOS transistor but with a much longer bulk portion.

Embodiment 12. The method according to any of embodiments 1-11, wherein the detector is placed in an edge-on fashion during imaging, such that the X-ray irradiation enters a side of a substrate of the detector.

Embodiment 13. The method according to embodiment 2, wherein the detector includes a plurality of potential wells,
wherein the X-ray irradiation enters a side of a substrate of the detector and travels through the substrate, interacting with local atoms and generating electrons within the substrate,
wherein a summation of the amount of charges in a plurality of the first potential wells encountered by the X-ray irradiation within the substrate provides one constraint of Formula 1.

Embodiment 14. The method according to embodiment 13, wherein repeating the determination of the generated charge density at a different thickness within the material of the detector includes changing the number of potential wells taken into account and recalculating the generated charge density within the detector using Formula 1.

Embodiment 15. The method according to embodiment 14, wherein the step of repeating the determination of the generated charge density at a different thickness within the material of the detector, by changing the number of potential wells taken into account and recalculating the generated charge density within the detector using Formula 1, is performed multiple times.

Embodiment 16. The method according to any of embodiments 13-15, wherein the method includes any of the features recited in any of embodiments 3-12.

Embodiment 17. The method according to any of embodiments 1-16, further comprising transferring charges from a substrate of the detector to an adjacent readout circuit.

Embodiment 18. The method according to embodiment 17, wherein transferring charges comprises using the same charge transfer approach that is used in a charge coupled device (CCD).

Embodiment 19. The method according to any of embodiments 17-18, wherein transferring charges comprises using a charge transfer logic as follows (see also FIG. 31):
i) at a first time (t1), a first voltage (v1) is set high and a second voltage (v2) and a third voltage (v3) are off or set very low;

ii) at a second time (t2), v1 and v2 are set high and v3 is off or set very low; and iii) at a third time (t3), v2 is set high and v1 and v3 are off or set very low.

Embodiment 20. The method according to embodiment 19, wherein the charge transfer logic further comprises:

iv) at a fourth time (t4), v2 and v3 are set high and v1 is off or set very low;

v) at a fifth time (t5), v3 is set high and v1 and v2 are off or set very low;

vi) at a sixth time (t6), v1 and v3 are set high and v2 is off or set very low; and vii) steps i) through vi) are repeated continuously such that charges under each gate in the detector are transferred to the right-most readout circuit (i.e., for the entire transferring of charges).

Embodiment 21. The method according to any of embodiments 1-20, wherein the sample is a part of a human patient (e.g., a body part).

Embodiment 22. The method according to any of embodiments 1-21, wherein the X-ray radiation has an energy of from 10 keV to 120 keV.

Embodiment 23. The method according to any of embodiments 1-21, wherein the X-ray radiation has an energy of less than 20 keV.

Embodiment 24. The method according to any of embodiments 1-21, wherein the X-ray radiation has an energy of more than 20 keV.

Embodiment 25. The method according to any of embodiments 1-24, wherein the detector includes a fixed thresholding detector.

Embodiment 26. The method according to any of embodiments 1-25, wherein the detector includes a dynamic thresholding detector.

Embodiment 27. The method according to any of embodiments 1-26, wherein the imaging is a computed tomography (CT) scan.

Embodiment 28. The method according to any of embodiments 1-27, wherein the X-ray radiation is provided by an X-ray source of a CT scanner.

Embodiment 29. The method according to embodiment 28, wherein the CT scanner has third-generation geometry.

Embodiment 30. The method according to embodiment 28, wherein the CT scanner has fourth-generation geometry.

Embodiment 31. The method according to any of embodiments 1-30, wherein the energy resolving process is performed by a processor.

Embodiment 32. The method according to any of embodiments 1-31, wherein the steps of the energy resolving process are stored on a (non-transitory) machine-readable medium (e.g., a computer-readable medium).

Embodiment 33. The method according to embodiment 32, wherein one or more processors executes the steps of the energy resolving process.

Embodiment 34. A (non-transitory) machine-readable medium (e.g., a computer-readable medium) having machine-executable (e.g., computer-executable) instructions for performing the energy resolving process described in any of embodiments 2-31.

Embodiment 35. An imaging system, comprising:

a computed tomography scanner including an X-ray source;

a detector for receiving X-ray radiation from the X-ray source after it passes through a sample to be imaged; and the machine-readable medium according to embodiment 34.

Embodiment 36. The system according to embodiment 35, wherein the detector is positioned in an edge-on fashion in relation to the X-ray source such that the X-ray radiation from the X-ray source enters a side of a substrate of the detector. a computed tomography Embodiment 37. The system according to any of embodiments 35-36, wherein the detector is a strip detector.

Embodiment 38. The system according to any of embodiments 35-37, wherein the detector is a semiconductor strip detector.

Embodiment 39. The system according to embodiment 38, wherein the semiconductor is silicon such that the detector is a silicon strip detector.

Embodiment 40. The system according to embodiment 38, wherein the semiconductor is cadmium telluride (CdTe).

Embodiment 41. The system according to embodiment 38, wherein the semiconductor is cadmium zinc telluride (CTZ).

Embodiment 42. The system according to embodiment 38, wherein the semiconductor is silicon, CdTe, or CTZ.

Embodiment 43. The system according to embodiment 39, wherein a bulk material of the silicon is p⁻ silicon.

Embodiment 44. The system according to any of embodiments 35-43, wherein the detector includes a plurality of potential wells.

Embodiment 45. The system according to any of embodiments 35-44, wherein the detector has a structure that mirrors that of a MOS transistor but with a much longer bulk portion.

Embodiment 46. The system according to any of embodiments 35-45, further comprising an analog-digital converter (ADC) for quantifying collected charges from the detector.

Embodiment 47. The method according to any of embodiments 1-33, further comprising quantifying collected charges using an analog-digital converter (ADC).

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

EXAMPLE 1

A simulation was performed on the detector depicted in FIG. 30. Semiconductor device simulation tool Silvaco Atlas was used for the simulation. The simulation procedure had multiple major steps. First, ten different monochromatic X-rays with energy ranging from 10 keV to 100 keV (in 10 keV increments) were applied on the silicon bulk; and then the beam intensity was increased stepwise from 1 W/cm² to 10 W/cm² to obtain the corresponding charge response; next, a composited X-ray, having the same spectrum as a real X-ray, was used as a beam source, and the energy distribution was derived from charge information in PWs. For the real X-ray simulation, a GE_Maxiray_125 tube was adopted as the X-ray source.

FIG. 32 shows a simulation image for the device modeling with net doping. Referring to FIG. 32, an overview of the 2D device model is depicted. In addition, the silicon substrate had a length of 9900 μm, which is long enough to fully assimilate photons under an energy of 20 keV and absorb a fraction of photons with energy over 20 keV. No constraint of the device thickness was used because radiation enters the device from the side of the bulk.

Because no charge was to be generated, when X-rays enter the depletion region, the width was at least larger than the depletion region when necessary bias was applied on the gate, and in this case, 5 μm was chosen. Similar to a CCD, a p⁻ type substrate was adopted in the simulation. Particularly, to minimize dark current generated by surface traps or defects, buried channel doping was introduced in the surface of the silicon bulk (FIG. 32 and Table 1). Buried channel efficiently reduces the side effects caused by surface defects as well as meliorates charge transfer inefficiency (CTI).

TABLE 1

Device details for Example 1

| | |
|---|---|
| Length | 9900 um (99 layers) |
| Width | 5 um |
| Electrode Length | 99 um |
| P type doping | 1e+15 per cm³ |
| N type channel | 1e+10 per cm³ |
| Applied bias | −5 V ~ +5 V |

When X-rays enter the device, electrons will be generated at different positions of the bulk in response to the radiation impulse. The fraction of photons being absorbed as a function of position is presented in FIG. 33 for different energies. Photon absorption rate degrades as photon energy increases. As universal X-ray can be regarded as a linear combination of radiations with different frequencies, responses of monochromatic radiations can then be substituted into Equation (10) to obtain an approximate solution.

When positive bias is applied on electrodes, a depletion region will form under the oxide layer. Generated electrons can then be collected in the depletion region under the force of electric field, as shown in FIG. 30. During the collection stage, a good device has the following properties: speed, accuracy, and integrity. Regarding speed, collection rate should be as fast as possible to match CT applications and can be related to bias and doping concentration. Regarding accuracy, during a limited time interval, charges collected in the PWs should be pure enough. Not all charges collected in PWs are generated by photons as there is a large fraction of electrons that are thermions caused by doping and intrinsic carriers (referred to as dark current). Regarding integrity, under ideal condition, all the photon-generated electrons should be collected in PWs for later analyzing and processing, because detected photon electrons directly correspond to the incident beam spectrum.

It is possible to minimize the influence of dark current by inducing contrast. If radiation is removed while bias is still working for the same time, then collected electrons under this condition can be regarded as thermions and net photon-generated electrons can be obtained by subtracting thermions. FIGS. 34A-34J provide the charge responses of monochromatic X-rays with energy from 10 keV to 100 keV, respectively, as a function of beam intensity. Simulation results show that generated charge density varies as intensity increases, and the relationship between them has the form of Equation (11).

$$Pe = kI + d \quad (11)$$

where Pe is collected electron density, k is determined by X-ray frequency, I is beam intensity, and d is a constant related to material property. As no photoelectron is generated without illumination, d is generated by dark current and had the value of $4 \times 10^{16} \text{cm}^{-3}$ in the simulation. Different thicknesses are required to fully assimilate X-ray with different energy; thus, k varies as photon energy and bulk thickness change and can be easily obtained from simulation. Actually, Equation (11) is a special case of monochromatic radiation of Equation (10), wherein the coefficient k contains factors of attenuation, photon energy, and photoelectron generating rate. For further analysis, it is also assumed that the substrate is horizontally uniform, which means that d is ideally proportional to thickness.

Before stepping to real X-ray response, a simple procedure of resolving energy distribution can be as follows. Three different types of composited beams can be applied on the structure, and each beam contains three different energy components. Next, the charge information of first n layers (n=1, 2, 3) can be extracted. Then, the extracted charge density can be substituted into Equation (12) and energy distribution I can be solved for.

$$\begin{bmatrix} k\_11 & k\_12 & k\_13 \\ k\_21 & k\_22 & k\_23 \\ k\_31 & k\_32 & k\_33 \end{bmatrix} \begin{bmatrix} I\_1 \\ I\_2 \\ I\_3 \end{bmatrix} + \begin{bmatrix} d\_1 \\ d\_2 \\ d\_3 \end{bmatrix} = \begin{bmatrix} g\_1 \\ g\_2 \\ g\_3 \end{bmatrix} \quad (12)$$

The simulation results are provided in Table 2.

TABLE 2

Simulation results of sample composited radiations

| Sim No. | Comp | Intensity | Separating Layer | Position | Charge Density | Resolved Intensity | Euclidean Distance |
|---|---|---|---|---|---|---|---|
| Exp1 | 10 keV | 1 w | 1 | L3 | 3.63E+17 | 0.99 w | 0.05 |
| | 20 keV | 2 w | 2 | L27 | 6.59E+17 | 2.02 w | |
| | 40 keV | 4 w | 3 | L99 | 1.27E+18 | 3.95 w | |
| Exp2 | 10 keV | 1 w | 1 | L3 | 3.24E+17 | 1.01 w | 0.02 |
| | 20 keV | 2 w | 2 | L27 | 5.64E+17 | 1.99 w | |
| | 60 keV | 4 w | 3 | L99 | 1.12E+18 | 3.98 w | |
| Exp3 | 15 keV | 1 w | 1 | L6 | 3.91E+17 | 0.76 w | 0.30 |
| | 30 keV | 2 w | 2 | L72 | 9.25E+17 | 1.89 w | |
| | 50 keV | 4 w | 3 | L99 | 1.19E+18 | 4.15 w | |

Layer thickness was not chosen arbitrarily, because it cannot be guaranteed that Equation (12) has non-trivial solutions. For example, if layer 1 is long enough to fully assimilate photons with energy 10 keV and 20 keV such that thus k_i1 s and k_i2 s are almost identical, matrix K can be singular. Although separation in this example experiment is not completely optimized, reasonable solutions can also be provided by referring FIG. 33. Resolved energy error is represented in Euclidean Distance. Note that Exp 3 suffers greater error, which comes from the limitation of bulk length that the best solution fell outside the structure in the simulation. As seen from the simulation results, the error of the solved spectrum is acceptable in comparison with original energy distribution, thus all proposed assumptions are reasonable and the energy resolving approach is useful and functional.

EXAMPLE 2

Example 1 was repeated, this time using an X-ray source with the same energy distribution as generated by GE Maxiray_125 tube, which is a real X-ray source. The spectrum of the GE_Maxiray_125 tube is shown in FIG. 35.

As the whole continuous spectrum is generally not needed for medical application, the given energy distribution in FIG. 35 was quantified into 10 discrete energies from 10 keV to 100 keV (10 keV increments). The quantified energy distribution is depicted in FIG. 36 and was used as criteria of the resolved value.

FIG. 37 shows a simulation image of a charged substrate in which photoelectrons are collected in potential wells (PWs). Dividing layers may not be optimized, and four discrete energies of 20 keV, 40 keV, 60 keV, and 80 keV were solved, so the data of four layers can be used to solve the corresponding energy distribution.

The whole device had a length of 9900 μm and was separated into 4 equal layers. The procedure of Example 1 was repeated, and data of the first 1, 2, 3, and 4 layers was substituted into the corresponding equation to obtain a unique solution of energy intensity of the given four energies. FIG. 38 shows this resolved energy distribution.

EXAMPLE 3

Charge transfer is the final stage before post-processing. Charge transfer of the device of Example 1 was simulated using the same parameters and software as in Example 1. FIGS. 39A-39C shows the charge transfer between two adjacent electrodes driven by the charge transfer logic. Referring to these figures, the simulation showed that it takes $1.05 \times 10^{-7}$ s to transfer the collected charge to the next PW, and transfer efficiency of 0.999985 was achieved. Under these conditions, the greatest charge information lost happens on the transferring of charges under first electrode which is $0.999985^{\wedge}100=0.9985$. Thus, error during transfer stage will not be greater than 2%, which is acceptable.

The result of monochromatic response is the infrastructure of the whole energy resolving theory that provides the process to obtain the exact k value (see Equation (10)). As the device is separated into more layers, enough values of k can be obtained and more precise energy distribution can be achieved. Theoretically, the energy resolving methods and devices of the subject invention are able to achieve infinite precision.

In the examples, the distributions of only four different energies were provided because the device in simulation was not completely optimized. As more energies are resolved, the result can be affected by errors caused by doping, dark current, and/or layer thickness.

A source of the error of results comes from the layer separation, as discussed in Example 2. Length limitation can also cause issues. Referring to FIG. 33, the attenuation curves of photons over 60 keV are fairly clustered together when device length is smaller than 1 cm, which means k values of these energies are pretty close. Some of the equations were nearly linearly dependent, which is not helpful to obtain good solutions.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Overdick, Michael; Baumer, Christian; Engel, K. J.; et al, "Status of Direct Conversion Detectors for Medical Imaging With X-Rays," in Nuclear Science, IEEE Transactions on, vol. 56, no. 4, pp. 1800-1809, August 2009.

Doran S J, Koerkamp K K, Bero M A, et al. A CCD-based optical CT scanner for high-resolution 3D imaging of radiation dose distributions: equipment specifications, optical simulations and preliminary results[J]. Physics in medicine and biology, 2001, 46(12): 3191.

Pan D, Roessl E, Schlomka J P, et al. Computed Tomography in Color: NanoK-Enhanced Spectral CT Molecular Imaging[J]. Angewandte Chemie, 2010, 122(50): 9829-9833.

Chu J, Cong W, Li L, et al. Combination of current-integrating/photon-counting detector modules for spectral CT[J]. Physics in medicine and biology, 2013, 58(19): 7009.

Taguchi K, Iwanczyk J S. Vision 20/20: Single photon counting x-ray detectors in medical imaging[J]. Medical physics, 2013, 40(10): 100901.

Bornefalk H, Danielsson M. Photon-counting spectral computed tomography using silicon strip detectors: a feasibility study[J]. Physics in medicine and biology, 2010, 55(7): 1999.

Persson M, Huber B, Karlsson S, et al. Energy-resolved CT imaging with a photon-counting silicon-strip detector[J]. Physics in medicine and biology, 2014, 59(22): 6709.

Gruner S M, Tate M W, Eikenberry E F. Charge-coupled device area X-ray detectors[J]. Review of Scientific Instruments, 2002, 73(8): 2815-2842.

Alvarez R E, Macovski A. Energy-selective reconstructions in x-ray computerised tomography[J]. Physics in medicine and biology, 1976, 21(5): 733.

Shikhaliev P M. Projection x-ray imaging with photon energy weighting: experimental evaluation with a prototype detector[J]. Physics in medicine and biology, 2009, 54(16): 4971.

Giersch J, Niederlohner D, Anton G. The influence of energy weighting on X-ray imaging quality[J]. Nuclear Instruments and Methods in Physics Research Section A: Accelerators, Spectrometers, Detectors and Associated Equipment, 2004, 531(1): 68-74.

Shikhaliev P M. Energy-resolved computed tomography: first experimental results[J]. Physics in medicine and biology, 2008, 53(20): 5595.

Taguchi K, Frey E C, Wang X, et al. An analytical model of the effects of pulse pileup on the energy spectrum recorded by energy resolved photon counting x-ray detectors[J]. Medical physics, 2010, 37(8): 3957-3969.

Burke, B. E.; Mountain, R. W.; Daniels, P. J.; et al, "CCD soft X-ray imaging spectrometer for the ASCA satellite," in Nuclear Science, IEEE Transactions on, vol. 41, no. 1, pp. 375-385, February 1994.

Lundqvist, M.; Cederstrom, B.; Chmill, V.; et al, "Computer simulations and performance measurements on a silicon strip detector for edge-on imaging," in Nuclear Science, IEEE Transactions on, vol. 47, no. 4, pp. 1487-1492, August 2000.

Bertolini G, Coche A. SEMICONDUCTOR DETECTORS [J]. 1968.

Marcelot, O.; Estribeau, M.; Goiffon, V.; et al, "Study of CCD Transport on CMOS Imaging Technology: Comparison Between SCCD and BCCD, and Ramp Effect on the CTI," in Electron Devices, IEEE Transactions on, vol. 61, no. 3, pp. 844-849, March 2014.

Tompsett, M. F., "Surface potential equilibration method of setting charge in charge-coupled devices," in Electron Devices, IEEE Transactions on, vol. 22, no. 6, pp. 305-309, June 1975.

Hoople, C. R.; Krusius, J. P., "Characteristics of submicrometer gaps in buried-channel CCD structures," in Electron Devices, IEEE Transactions on, vol. 38, no. 5, pp. 1175-1181, May 1991.

Arfelli, F.; Barbiellini, G.; Bonvicini, V.; et al, "An "edge-on" silicon strip detector for X-ray imaging," in Nuclear Science, IEEE Transactions on, vol. 44, no. 3, pp. 874-880, June 1997.

L. Rigon, F. Arfelli, A. Astolfo, et al. A single-photon counting "edge-on" silicon detector for synchrotron radiation mammography, Nuclear Instruments and Methods in Physics Research Section A: Accelerators, Spectrometers, Detectors and Associated Equipment, Volume 608, Issue 1, Supplement, 1 September 2009, Pages S62-S65.

What is claimed is:

1. A method of imaging, comprising:
   providing X-ray radiation to a sample to be imaged;
   collecting the X-ray radiation with a detector; and
   performing an energy resolving process on collected charges of the collected X-ray radiation,
   wherein the detector comprises a plurality of potential wells,
   wherein the detector is placed in an edge-on fashion during imaging, such that the X-ray radiation enters a side of a substrate of the detector,
   wherein the X-ray radiation enters a side of a substrate of the detector and travels through the substrate, interacting with local atoms and generating electrons within the substrate, and
   wherein a summation of an amount of charges in the plurality of potential wells encountered by the X-ray radiation within the substrate provides one constraint of the energy resolving process.

2. The method according to claim 1, wherein the energy resolving process includes:
   determining the generated charge density within the detector using Formula 1:

$$m_1 E_1 N_1 a_{k1} + m_2 E_2 N_2 a_{k2} + \ldots + M_n E_n N_n a_{kn} = g_k(x) \quad \text{Formula 1}$$

where $E_i$ is photon energy, $N_i$ is photon density with energy $E_i$ $a_{ki}$ is the attenuation coefficient of photon with energy $E_i$ for the given material thickness, $m_i$ is an empirical coefficient that represents the number of generated charges by photons with energy $E_i$ per energy unit, and $g_k(x)$ is the generated charge density within the material of the detector of a specific thickness; and
   repeating the determination of the generated charge density at a different thickness within the material of the detector.

3. The method according to claim 2, wherein repeating the determination of the generated charge density at a different thickness within the material of the detector includes changing the number of potential wells taken into account and recalculating the generated charge density within the detector using Formula 1.

4. The method according to claim 3, wherein the step of repeating the determination of the generated charge density at a different thickness within the material of the detector, by changing the number of potential wells taken into account and recalculating the generated charge density within the detector using Formula 1, is performed multiple times.

5. The method according to claim 1, wherein the detector is a semiconductor strip detector.

6. The method according to claim 5, wherein the semiconductor is silicon, cadmium telluride (CdTe), or cadmium zinc telluride (CTZ).

7. The method according to claim 1, further comprising transferring charges from a substrate of the detector to an adjacent readout circuit,
   wherein transferring charges comprises using a charge transfer logic as follows:
   i) at a first time (t1), a first voltage (v1) is set high and a second voltage (v2) and a third voltage (v3) are off or set very low;
   ii) at a second time (t2), v1 and v2 are set high and v3 is off or set very low; and
   iii) at a third time (t3), v2 is set high and v1 and v3 are off or set very low.

8. The method according to claim 7, wherein the charge transfer logic further comprises:
   iv) at a fourth time (t4), v2 and v3 are set high and v1 is off or set very low;
   v) at a fifth time (t5), v3 is set high and v1 and v2 are off or set very low;
   vi) at a sixth time (t6), v1 and v3 are set high and v2 is off or set very low; and
   vii) steps i) through vi) are repeated continuously such that charges under each gate in the detector are transferred to the right-most readout circuit.

9. The method according to claim 1, further comprising quantifying collected charges using an analog-digital converter (ADC).

10. The method according to claim 1, wherein the X-ray radiation has an energy of from 10 keV to 120 keV.

11. The method according to claim 1, wherein the detector includes at least one of a fixed thresholding detector and a dynamic thresholding detector.

12. The method according to claim 1, wherein the imaging is a computed tomography (CT) scan, and
   wherein the X-ray radiation is provided by an X-ray source of a CT scanner.

13. The method according to claim 12, wherein the CT scanner has third-generation geometry or fourth-generation geometry.

14. An imaging system, comprising:
   a computed tomography scanner including an X-ray source;
   a detector for receiving X-ray radiation from the X-ray source after it passes through a sample to be imaged;
   a processor; and
   a non-transitory machine-readable medium in operable communication with the processor and having machine-executable instructions stored thereon that, when executed by the processor, perform the following energy resolving process;
   determining a generated charge density within the detector using Formula 1:

$$m_1 E_1 N_1 a_{k1} + m_2 E_2 N_2 a_{k2} + \ldots + M_n E_n N_n a_{kn} = g_k(x) \quad \text{Formula 1}$$

where $E_i$ is photon energy, $N_i$ is photon density with energy $E_i$, $a_{ki}$ is the attenuation coefficient of photon with energy $E_i$ for the given material thickness, $m_i$ is an empirical coefficient that represents the number of generated charges by photons with energy $E_i$ per energy unit, and $g_k(x)$ is the generated charge density within the material of the detector of a specific thickness; and repeating the determination of the generated charge density at a different thickness within the material of the detector.

15. The system according to claim 14, wherein the detector is positioned in an edge-on fashion in relation to the X-ray source such that the X-ray radiation from the X-ray source enters a side of a substrate of the detector.

16. The system according to claim 14, wherein the detector is a semiconductor strip detector, and wherein the semiconductor is silicon, cadmium telluride (CdTe), or cadmium zinc telluride (CTZ).

17. The system according to claim 14, wherein the detector comprises a plurality of potential wells,
   wherein the system further comprises an analog-digital converter (ADC) for quantifying collected charges from the detector, and
   wherein the CT scanner has third-generation geometry or fourth-generation geometry.

18. A method of imaging, comprising:
   providing X-ray radiation to a sample to be imaged;
   collecting the X-ray radiation with a detector; and
   performing an energy resolving process on collected charges of the collected X-ray radiation;
   transferring charges from a substrate of the detector to an adjacent readout circuit,
   wherein transferring charges comprises using a charge transfer logic as follows:
      i) at a first time (t1), a first voltage (v1) is set high and a second voltage (v2) and a third voltage (v3) are off or set very low;
      ii) at a second time (t2), v1 and v2 are set high and v3 is off or set very low; and
      iii) at a third time (t3), v2 is set high and v1 and v3 are off or set very low.

19. The method according to claim 18, wherein the charge transfer logic further comprises:
   iv) at a fourth time (t4), v2 and v3 are set high and v1 is off or set very low;
   v) at a fifth time (t5), v3 is set high and v1 and v2 are off or set very low;
   vi) at a sixth time (t6), v1 and v3 are set high and v2 is off or set very low; and vii) steps i) through vi) are repeated continuously such that charges under each gate in the detector are transferred to the right-most readout circuit.

20. The method according to claim 18, wherein the energy resolving process includes:
   determining the generated charge density within the detector using Formula 1:

$$m_1 E_1 N_1 a_{k1} + m_2 E_2 N_2 a_{k2} + \ldots + M_n E_n N_n a_{kn} = g_k(x) \quad \text{Formula 1}$$

where $E_i$ is photon energy, $N_i$ is photon density with energy $E_i$, $a_{ki}$ is the attenuation coefficient of photon with energy $E_i$ for the given material thickness, $m_i$ is an empirical coefficient that represents the number of generated charges by photons with energy $E_i$ per energy unit, and $g_k(x)$ is the generated charge density within the material of the detector of a specific thickness; and
   repeating the determination of the generated charge density at a different thickness within the material of the detector.

21. The method according to claim 20, wherein the detector comprises a plurality of potential wells,
   wherein the X-ray radiation enters a side of a substrate of the detector and travels through the substrate, interacting with local atoms and generating electrons within the substrate, and
   wherein a summation of an amount of charges in the plurality of potential wells encountered by the X-ray radiation within the substrate provides one constraint of Formula 1.

22. The method according to claim 20, wherein repeating the determination of the generated charge density at a different thickness within the material of the detector includes changing the number of potential wells taken into account and recalculating the generated charge density within the detector using Formula 1.

23. The method according to claim 20, wherein the step of repeating the determination of the generated charge density at a different thickness within the material of the detector, by changing the number of potential wells taken into account and recalculating the generated charge density within the detector using Formula 1, is performed multiple times.

24. The method according to claim 20, wherein the detector comprises a plurality of potential wells,
   wherein the system further comprises an analog-digital converter (ADC) for quantifying collected charges from the detector, and
   wherein the CT scanner has third-generation geometry or fourth-generation geometry.

* * * * *